United States Patent
Ishino et al.

(10) Patent No.: US 7,977,405 B2
(45) Date of Patent: Jul. 12, 2011

(54) POLYMERIZABLE MONOMER-CONTAINING COMPOSITION

(75) Inventors: Hiroshige Ishino, Kurashiki (JP); Takahiro Sekiguchi, Kurashiki (JP); Koichi Okada, Kurashiki (JP); Naoki Nishigaki, Kurashiki (JP)

(73) Assignee: Kurray Medical Inc., Kurashiki-shi (JP)

( * ) Notice: Subject to any disclaimer, the term of this patent is extended or adjusted under 35 U.S.C. 154(b) by 0 days.

(21) Appl. No.: 12/523,538

(22) PCT Filed: Jan. 16, 2008

(86) PCT No.: PCT/JP2008/050437
§ 371 (c)(1),
(2), (4) Date: Oct. 23, 2009

(87) PCT Pub. No.: WO2008/087979
PCT Pub. Date: Jul. 24, 2008

(65) Prior Publication Data
US 2010/0036075 A1    Feb. 11, 2010

(30) Foreign Application Priority Data

Jan. 17, 2007 (JP) ................. 2007-008420
Jan. 17, 2007 (JP) ................. 2007-008421
Mar. 20, 2007 (JP) ................. 2007-073603

(51) Int. Cl.
C08F 118/02 (2006.01)
C08L 33/02 (2006.01)
A61K 6/083 (2006.01)

(52) U.S. Cl. ........ 523/116; 526/320; 524/556; 524/558; 524/854

(58) Field of Classification Search .......... 526/320, 526/321, 323.1, 323.2; 523/116; 524/556, 524/558, 854
See application file for complete search history.

(56) References Cited

U.S. PATENT DOCUMENTS

| | | | |
|---|---|---|---|
| 4,719,297 | A | 1/1988 | Henne et al. |
| 5,204,383 | A | 4/1993 | Manabe et al. |
| 5,399,770 | A | 3/1995 | Leppard et al. |
| 5,539,017 | A | 7/1996 | Rheinberger et al. |
| 5,648,441 | A | 7/1997 | Keller et al. |
| 5,942,290 | A | 8/1999 | Leppard et al. |
| 6,107,358 | A | 8/2000 | Harada et al. |
| 2004/0005524 | A1 | 1/2004 | Oxman et al. |
| 2005/0042363 | A1 | 2/2005 | Kukhtin et al. |
| 2005/0256221 | A1 | 11/2005 | Zeng et al. |
| 2009/0258966 | A1* | 10/2009 | Hirayama et al. ............ 523/118 |

FOREIGN PATENT DOCUMENTS

| | | |
|---|---|---|
| EP | 0 009 348 | 7/1983 |
| JP | 57 197289 | 12/1982 |
| JP | 64 90277 | 4/1989 |
| JP | 3 279307 | 12/1991 |
| JP | 5 345790 | 12/1993 |
| JP | 6 234939 | 8/1994 |
| JP | 7 258018 | 10/1995 |
| JP | 9 3109 | 1/1997 |
| JP | 10 95788 | 4/1998 |
| JP | 10 245525 | 9/1998 |
| JP | 10 251310 | 9/1998 |
| JP | 2000 53519 | 2/2000 |
| JP | 2000 159621 | 6/2000 |
| JP | 2003 96122 | 4/2003 |
| JP | 2004 43427 | 2/2004 |
| JP | 2004 91949 | 3/2004 |
| JP | 2005 171213 | 6/2005 |
| JP | 2005 531632 | 10/2005 |
| WO | 2004 047773 | 6/2004 |

OTHER PUBLICATIONS

Machine Translation of JP 2004-026838.*
Lou, Xia et al., "Hydrophilic Sponges Based on 2-Hydroxyethyl Methacrylate. IV. Novel Synthetic Routes to Hydroxyl-Containing Crosslinking Agents and Their Effect on the Mechanical Strength of Sponges", International Journal of Polymeric Materials, vol. 37, No. 1-2, pp. 1-14, (Jun. 12, 1997).
Horak, D. et al., "A novel hydrophilic crosslinker in preparation of hydrophilic sorbents", Reactive & Functional Polymers, vol. 32, pp. 277-280, (May 28, 1997).
Obata, Makoto et al., "Chirality Induction in Cyclopolymerization. 8. Cyclocopolymerization of 1,2:5,6-Di-O-isopropylidene-3,4-di-O-methacryloyl-D-mannitol with Styrene", Macromolecules, vol. 30, No. 3, pp. 348-353, (1997).
U.S. Appl. No. 12/523,554, filed Jul. 17, 2009, Hinamoto, et al.
U.S. Appl. No. 12/523,546, filed Jul. 17, 2009, Ishino, et al.
U.S. Appl. No. 12/523,591, filed Jul. 17, 2009, Ishino, et al.
U.S. Appl. No. 12/532,289, filed Sep. 21, 2009, Sekiguchi.

* cited by examiner

*Primary Examiner* — David Wu
*Assistant Examiner* — Vu A Nguyen
(74) *Attorney, Agent, or Firm* — Oblon, Spivak, McClelland, Maier & Neustadt, L.L.P.

(57) ABSTRACT

The present invention provides a composition suitable for a dental composition. The present invention is a composition containing: a polymerizable monomer (A) having an unconjugated carbon chain with at least four carbon atoms bonded continuously, at least two polymerizable groups, and at least two hydroxyl groups; and a polymerizable monomer (B) having one polymerizable group and at least one hydroxyl group. When a suitable component is added to this composition, the resultant composition can be used suitably for dental materials such as a primer, bonding material, composite resin, and cement.

24 Claims, No Drawings

POLYMERIZABLE MONOMER-CONTAINING COMPOSITION

This application is a 371 of PCT/JP08/50437, filed Jan. 16, 2008.

TECHNICAL FIELD

The present invention relates to a composition containing: a bifunctional polymerizable monomer having a plurality of polymerizable groups and hydroxyl groups; and a monofunctional polymerizable monomer having one polymerizable group and at least one hydroxyl group.

BACKGROUND ART

When a lost part of a tooth is filled or covered with a restorative material, generally a dental adhesive is used. A known dental adhesive is one containing a polymerizable monomer having a polymerizable group and a hydroxyl group.

For example, WO 2004/047773 describes a dental adhesive composition characterized by containing a polyfunctional polymerizable monomer that is an ester compound of polyhydric alcohol having 3 to 6 carbon atoms and a plurality of (meth)acrylic acids and that has one to two hydroxyl groups, a monofunctional (meth)acrylate having no hydroxyl group in the molecule, a polymerizable monomer having an acidic group in the molecule, an organoboron compound as a curing agent, and a filling material. This describes that the addition of a small amount of the above polyfunctional polymerizable monomer to the composition can improve the cure rate considerably almost without affecting the adhesive properties of the composition, physical properties of the cured product, or operable time. This composition is, however, not necessarily excellent in penetrability into a collagen layer of dentin and may cause a reduction in bond strength, and therefore improvement in this respect has been desired.

When such a dental adhesive is allowed to act on dentin, it is important for the dental adhesive to have an decalcifying effect that allows a dentin surface to be dissolved with an acidic component, a penetration effect that allows a monomer component to penetrate into a collagen layer of dentin, and a curing effect that allows the monomer component thus penetrated to solidify to form a hybrid layer (hereinafter also referred to as a "resin-impregnated layer") with collagen.

It has been studied so far to simplify the form of application of the dental adhesive from a three-component three-step type in which the aforementioned decalcifying effect, penetration effect, and curing effect are applied sequentially, to a two-component two-step type in which the decalcifying effect and the penetration effect are integrated, and further to a one-component one-step type in which the decalcifying effect, penetration effect, and curing effect are all combined together. All the forms of application require compositions that can be used for dental adhesives that are excellent in adhesive properties.

DISCLOSURE OF THE INVENTION

The present invention has been made in order to solve the above-mentioned problems, and it is an object of the present invention to provide a composition that is suitable for dental compositions and that contains: a bifunctional polymerizable monomer having polymerizable groups and hydroxyl groups; and a monofunctional polymerizable monomer having one polymerizable group and at least one hydroxyl group.

The present invention is a composition containing: a polymerizable monomer (A) having an unconjugated carbon chain with at least four carbon atoms bonded continuously, at least two polymerizable groups, and at least two hydroxyl groups; and a polymerizable monomer (B) having one polymerizable group and at least one hydroxyl group.

In the present invention, it is preferable that the polymerizable monomer (A) have a group represented by formula (1):

[Chemical Formula 1]

where G is a hydroxyl group or polymerizable group and "*" indicates a bond.

Preferably, the polymerizable groups each are a group represented by formula (2), (3), or (4):

[Chemical Formula 2]

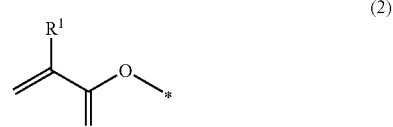

[Chemical Formula 3]

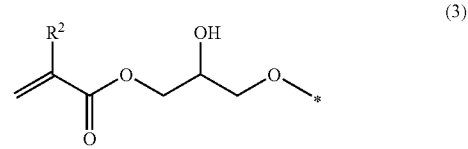

[Chemical Formula 4]

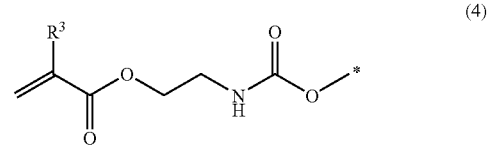

where $R^1$, $R^2$, and $R^3$ each indicate a hydrogen atom or an aliphatic hydrocarbon group having 1 to 10 carbon atoms and "*" indicates a bond.

Preferably, the polymerizable monomer (A) is a compound represented by formula (5):

[Chemical Formula 5]

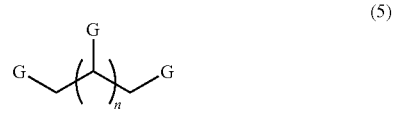

where Gs are hydroxyl groups or polymerizable groups, n is an integer of 2 or more, at least two of the Gs are hydroxyl groups, and at least two of the Gs are polymerizable groups. An example of more preferable polymerizable monomers (A) is a compound represented by formula (6):

[Chemical Formula 6]

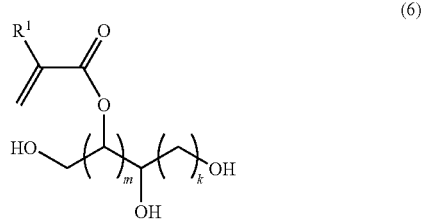
(6)

where $R^1$ denotes a hydrogen atom or an aliphatic hydrocarbon group having 1 to 10 carbon atoms, m denotes an integer of 2 or more, k denotes an integer of 1 or more, and the sequence order of m units having an ester group and k units having a hydroxyl group is arbitrary. In this case, it is preferable that m be 2 to 5 and k be 1 to 5.

Another example of more preferable polymerizable monomers (A) is a compound represented by formula (7):

[Chemical Formula 7]

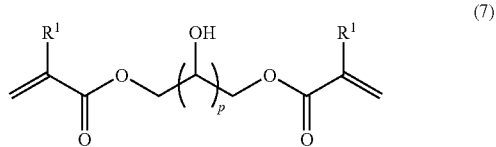
(7)

where $R^1$ denotes a hydrogen atom or an aliphatic hydrocarbon group having 1 to 10 carbon atoms and p denotes an integer of 2 or more. In this case, it is preferable that p be 2 to 4.

In the above, it is preferable that $R^1$ be a hydrogen atom or methyl group.

Preferably, the polymerizable monomer (B) is a compound represented by formula (8):

[Chemical Formula 8]

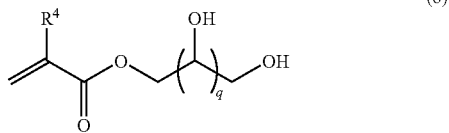
(8)

where $R^4$ indicates a hydrogen atom or an aliphatic hydrocarbon group having 1 to 10 carbon atoms and q denotes an integer of 0 or more. In this case, it is preferable that q be an integer of 0 to 4, and more preferably 0. It also is preferable that $R^4$ be a hydrogen atom or methyl group.

Preferably, the composition of the present invention contains 1 to 98 parts by weight of the polymerizable monomer (A) in 100 parts by weight of the whole amount of polymerizable monomer components. It is preferable that 2 to 5000 parts by weight of the polymerizable monomer (B) be contained with respect to 100 parts by weight of the polymerizable monomer (A). It is preferable that 1 to 90 parts by weight of a polymerizable monomer (C) having an acidic group be further contained in 100 parts by weight of the whole amount of polymerizable monomer components. It is preferable that 1 to 90 parts by weight of a crosslinkable polymerizable monomer (D) be further contained in 100 parts by weight of the whole amount of polymerizable monomer components.

Preferably, the composition of the present invention contains 1 to 2000 parts by weight of a solvent (E) with respect to 100 parts by weight of the whole amount of polymerizable monomer components. Preferably, the solvent (E) is a water-soluble solvent. It is preferable that 0.001 to 30 parts by weight of a polymerization initiator (F) be contained with respect to 100 parts by weight of the whole amount of polymerizable monomer components. It is preferable that 0.001 to 30 parts by weight of a polymerization accelerator (G) be contained with respect to 100 parts by weight of the whole amount of polymerizable monomer components. It is preferable that 1 to 2000 parts by weight of a filler (H) be contained with respect to 100 parts by weight of the whole amount of polymerizable monomer components.

Since the composition of the present invention contains: a polymerizable monomer (A) having a plurality of polymerizable groups and a plurality of hydroxyl groups; and a monofunctional polymerizable monomer (B) having one polymerizable group and at least one hydroxyl group, it is a composition that exhibits excellent curability and adhesive properties in various applications including dental applications. In particular, since the composition of the present invention has high penetrability into a collagen layer of dentin as well as high bond strength and bond durability with respect to a tooth structure (particularly dentin), it can be used suitably as a dental composition.

Furthermore, from another aspect, the present invention is a primer, bonding material, composite resin, or cement, each using the above-mentioned dental compositions. These dental materials exhibit excellent bond strength and bond durability with respect to a tooth structure (particularly dentin).

BEST MODE FOR CARRYING OUT THE INVENTION

The composition of the present invention contains: a bifunctional polymerizable monomer (A) having polymerizable groups and hydroxyl groups; and a monofunctional polymerizable monomer (B) having one polymerizable group and at least one hydroxyl group, and it is useful as a dental composition. In the present invention, terms "monofunctional", "bifunctional", and "trifunctional" are used and the terms "monofunctional", "bifunctional", and "trifunctional" indicate that one, two, and three polymerizable groups each are contained in one molecule.

Polymerizable Monomer (A)

The polymerizable monomer (A) has an unconjugated carbon chain with at least four carbon atoms bonded continuously, at least two polymerizable groups, and at least two hydroxyl groups. For the polymerizable monomer (A), polymerizable monomers that satisfy such a definition can be used independently or two or more of them can be used in combination.

The polymerizable monomer (A) has at least two polymerizable groups. When a composition of the present invention is used for a dental application, these polymerizable groups are polymerized and thereby the composition is cured to be able to function as dental materials such as a primer, bonding material, composite resin, or cement. Furthermore, since the number of the polymerizable groups is two or more, the polymerizable monomer (A) has crosslinkability. Accordingly, the composition has high curability and the cured product has high mechanical strength.

With respect to the polymerizable monomer (A), the polymerizable group denotes a group including a radical polymerizable functional group and examples thereof include a group including a vinyl group. Particularly, from the viewpoint of polymerization reactivity, the group represented by the following formula (2), (3), or (4) is preferable as the polymerizable group. Among these, from the viewpoint of ease of introduction into the polymerizable monomer (A), a group represented by formula (2) is most preferable.

[Chemical Formula 9]

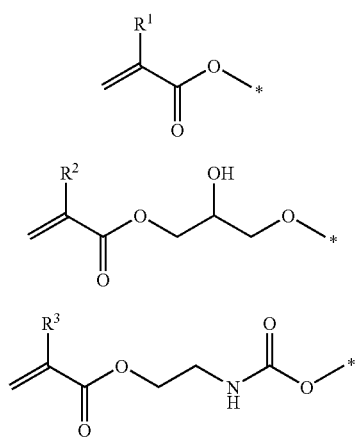

(2)

(3)

(4)

In the above formulae, $R^1$, $R^2$, and $R^3$ each indicate a hydrogen atom or an aliphatic hydrocarbon group having 1 to 10 carbon atoms and "*" indicates a bond. Examples of the aliphatic hydrocarbon group having 1 to 10 carbon atoms include an alkyl group having 1 to 10 carbon atoms, an alkenyl group having 2 to 10 carbon atoms, and an alkynyl group having 2 to 10 carbon atoms.

The alkyl group having 1 to 10 carbon atoms may be any one of linear, branched, and cyclic, and examples thereof include a methyl group, ethyl group, n-propyl group, isopropyl group, cyclopropyl group, n-butyl group, isobutyl group, sec-butyl group, tert-butyl group, cyclobutyl group, n-pentyl group, isopentyl group, neopentyl group, tert-pentyl group, cyclopentyl group, n-hexyl group, isohexyl group, cyclohexyl group, n-heptyl group, cycloheptanyl group, n-octyl group, 2-ethylhexyl group, cyclooctanyl group, n-nonyl group, cyclononanyl group, and n-decyl group.

The alkenyl group having 2 to 10 carbon atoms may be any one of linear, branched, and cyclic, and examples thereof include a vinyl group, allyl group, methylvinyl group, propenyl group, butenyl group, pentenyl group, hexenyl group, cyclopropenyl group, cyclobutenyl group, cyclopentenyl group, and cyclohexenyl group.

The alkynyl group having 2 to 10 carbon atoms may be any one of linear, branched, and cyclic, and examples thereof include ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, and 1-ethyl-3-butynyl.

When the polymerizable monomer (A) is used in, for example, dental applications, radical polymerization is performed. Accordingly, it is preferable from the viewpoint of radical polymerization reactivity of the final product that $R^1$, $R^2$, and $R^3$ each be a hydrogen atom or a methyl group. Furthermore, when the polymerizable monomer (A) is used in a dental composition, the polymerizable group may be detached from the polymerizable monomer (A) by, for example, hydrolysis. When the stimulativeness of the detached polymerizable group to a biological body is taken into account, it is preferable that the polymerizable group include a methacryloyloxy group. Therefore, it is more preferable that $R^1$, $R^2$, and $R^3$ each be a methyl group.

The polymerizable monomer (A) includes at least two polymerizable groups, and the at least two polymerizable groups may be identical to or different from each other.

The polymerizable monomer (A) has at least two hydroxyl groups. These hydroxyl groups allow the polymerizable monomer (A) to be provided with high hydrophilicity to have high penetrability into a collagen layer of dentin, which results in high adhesive properties of the composition to a tooth structure.

The polymerizable monomer (A) has an unconjugated carbon chain with at least four carbon atoms bonded continuously. Preferably, this carbon chain composes the whole or a part of the skeleton of the polymerizable monomer (A), and the polymerizable groups and hydroxyl groups are bonded to the carbon chain.

An example of the polymerizable monomer (A) is a compound in which a part of hydroxyl groups of a tetravalent or more alcohol compound having an unconjugated carbon chain with at least four carbon atoms bonded continuously is substituted by polymerizable groups so that the number of each of the hydroxyl groups and the polymerizable groups is two or more. Examples of the tetravalent or more alcohol compound having an unconjugated carbon chain with at least four carbon atoms bonded continuously are not particularly limited. Preferable examples thereof include sugar alcohol, monosaccharides, disaccharides, and trisaccharides, each of which has 4 to 20 carbon atoms. Examples of the sugar alcohol that is used preferably include erythritol, a sugar alcohol having 4 carbon atoms, xylitol, ribitol, and arabinitol, each of which is a sugar alcohol having 5 carbon atoms, mannitol, sorbitol, and iditol, each of which is a sugar alcohol having 6 carbon atoms, and maltitol, a sugar alcohol having 12 carbon atoms. Furthermore, glucamine, a sugar alcohol containing an amino group, also is used preferably. Examples of monosaccharides that are used preferably include xylose, ribose, arabinose, and lyxose, each of which is a monosaccharide having 5 carbon atoms, as well as glucose, mannose, galactose, sorbose, and fructose, each of which is a monosaccharide having 6 carbon atoms. Furthermore, glucosamine, mannosamine, galactosamine, N-acetylglucosamine, N-acetylmannosamine, and N-acetylgalactosamine that are monosaccharides, each of which contains an amino group and a derivative thereof, also are used preferably. Examples of disaccharides that are used preferably include trehalose, sucrose, maltose, lactose, and cellobiose. Examples of trisaccharides that are used preferably include Coupling Sugar (registered trademark), lactosucrose, maltotriose, and isomaltotriose. The composition of the present invention is used preferably as a dental composition and more preferably as a dental adhesive composition. From the viewpoint of adhesive properties to a tooth structure (particularly dentin), it is preferable that it have high penetrability into the tooth structure (particularly dentin). From such a viewpoint, the carbon number of the aforementioned alcohol compound is more preferably 4 to 15, further preferably 4 to 9, and particularly preferably 4 to 7. Moreover, from the same viewpoint, the number of the hydroxyl groups of the alcohol compound is preferably 4 to 15, more preferably 4 to 9, and particularly preferably 4 to 7. Specific examples of preferable alcohol compounds include: erythritol, mannitol, sorbitol, and maltitol as sugar alcohols; glucose and glucosamine as monosaccharides; trehalose and maltose as disaccharides; and maltotriose as trisaccharides. Among these, erythritol, mannitol, glucose, and trehalose are further preferable and erythritol and mannitol are particularly preferable.

Preferably, the polymerizable monomer (A) has a group represented by the following formula (1). This group is a structure that is characteristic to the compounds indicated above as examples.

[Chemical Formula 12]

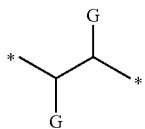

(1)

In the above formula, G indicates a hydroxyl group or polymerizable group and "*" indicates a bond.

With respect to the structure of the polymerizable monomer (A), specifically, the polymerizable monomer (A) is preferably a compound represented by formula (5).

[Chemical Formula 13]

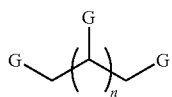

(5)

In the above formula, Gs are hydroxyl groups or polymerizable groups, n is an integer of 2 or more, at least two of the Gs are hydroxyl groups, and at least two of the Gs are polymerizable groups.

In this structure, the polymerizable group or the hydroxyl group is bonded to each carbon atom of the carbon chain, and therefore the polymerizable groups and hydroxyl groups are closely-located with a high density. Accordingly, when a composition containing this polymerizable monomer (A) is applied as a dental material, it exhibits excellent curability and adhesive properties. Furthermore, it also has an advantage that it can be produced easily using sugar alcohol.

From the viewpoints of curability and adhesive properties to a tooth structure of the composition as well as availability of raw materials, n is preferably an integer of 2 to 18, more preferably an integer of 2 to 9, and most preferably an integer of 2 to 4.

When adhesive properties to a tooth structure of the composition is considered important, the polymerizable monomer (A) is preferably a compound represented by the following formula (6).

[Chemical Formula 14]

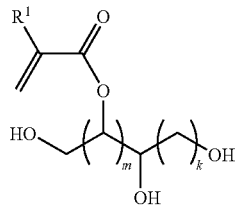

(6)

In the above formula, $R^1$ denotes the same as described above, m denotes an integer of 2 or more, k denotes an integer of 1 or more, and the sequence order of m units having an ester group and k units having a hydroxyl group is arbitrary.

From the viewpoints of curability and adhesive properties to a tooth structure of the composition as well as availability of raw materials, m is preferably 2 to 5, more preferably 2 to 4, and most preferably 2. Furthermore, k is preferably 1 to 5, more preferably 2 to 4, and most preferably 2. The total of m and k is preferably 3 to 18, more preferably 3 to 9, further preferably 4 to 8, and most preferably 4.

The compound represented by formula (6) has at least three hydroxyl groups, two of which are primary hydroxyl groups. These primary hydroxyl groups are highly advantageous for interaction with a tooth structure (particularly dentin). Accordingly, when a composition containing a compound represented by formula (6) is applied as dental applications, a composition with particularly high adhesive properties to a tooth structure (particularly dentin) is obtained. Moreover, since at least two groups represented by formula (2) are included as polymerizable groups, curability also is excellent.

Furthermore, among the compounds represented by formula (6), compounds represented by formulae (9) and (10) are preferable from the viewpoints of curability and adhesive properties to a tooth structure of the composition.

[Chemical Formula 15]

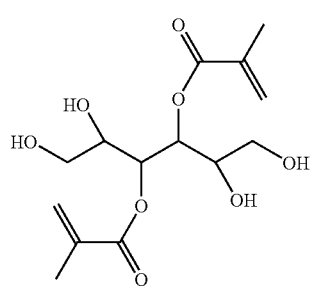

(9)

[Chemical Formula 16]

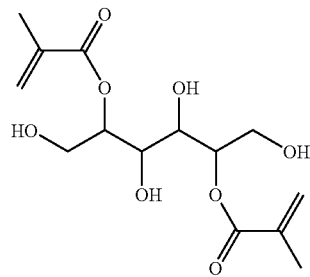

(10)

On the other hand, when curability of the composition is considered important, the polymerizable monomer (A) is preferably a compound represented by the following formula (7).

[Chemical Formula 17]

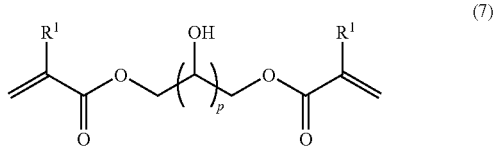

In the above formula, $R^1$ denotes the same as described above, and p denotes an integer of 2 or more.

The compound represented by formula (7) has polymerizable groups represented by formula (2) at the both ends of an unconjugated carbon chain with at least four carbon atoms bonded continuously and has particularly high polymerization performance due to a steric factor. Accordingly, when a composition containing a compound represented by formula (7) is applied as a dental application, it serves as a composition with particularly high curability. Moreover, since it has a plurality of hydroxyl groups, it has excellent penetrability into a collagen layer of dentin as well as excellent adhesive properties to a tooth structure.

p is preferably 2 to 4. This is because when a decomposition product is produced by an action such as hydrolysis inside an oral cavity, the decomposition product is a highly safe compound such as erythritol, xylitol, sorbitol, or mannitol. Examples of compounds in which p is 2 to 4 include erythritol di(meth)acrylate, xylitol di(meth)acrylate, and sorbitol di(meth)acrylate. Furthermore, erythritol di(meth)acrylate in which p is 2 is more preferable, and when the aforementioned viewpoints of polymerizability and stimulativeness to a biological body also are taken into consideration, erythritol dimethacrylate represented by the following general formula (11) is most preferable.

[Chemical Formula 18]

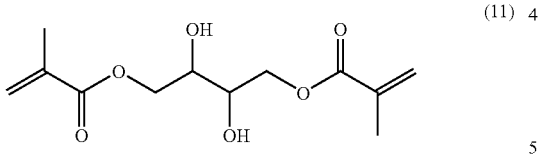

The polymerizable monomer (A) can be obtained through production by a known method. Specifically, for example, a carboxylic acid having a polymerizable group (for instance, a carboxylic acid in which a hydrogen atom is bonded to a bond of a group represented by formula (2)) or a derivative thereof and the tetravalent or more alcohol compound having an unconjugated carbon chain with at least four carbon atoms bonded continuously may be allowed to undergo an esterification reaction according to a conventional method and this may then be purified by a separation means such as chromatography. In order to improve the yield, the esterification reaction may be carried out after the carboxylic acid having a polymerizable group is converted into a derivative such as an acid halide.

When the polymerizable monomer (A) is particularly a compound represented by formula (6), especially a compound represented by formula (9) or (10), it is preferable that the polymerizable monomer (A) be produced by performing a step (a) where using a compound in which primary hydroxyl groups of the alcohol compound are protected beforehand, as a raw material, the compound and carboxylic acid having a polymerizable group (in this case, carboxylic acid in which a hydrogen atom is bonded to a bond of a group represented by formula (2)) or a derivative thereof are esterified, and a step (b) where the protecting groups of the primary hydroxyl groups of the resultant ester compound are deprotected. The derivative of the carboxylic acid having a polymerizable group is not particularly limited but an acid halide or acid anhydride is used preferably. When the reactivity with the alcohol compound is taken into account, an acid halide is used more preferably. Furthermore, among the acid halides, acid chloride is used particularly preferably when availability and storage stability of the compound are taken into account. The production process including these steps allows a polymerizable monomer to be obtained with high yield and therefore is suitable for industrial production.

The compound in which primary hydroxyl groups of the alcohol compound are protected beforehand can be obtained as a commercially available product, for example, 1,2:5,6-di-O-isopropylidene-D-mannitol and 1,3:4,6-di-O-benzylidene-D-mannitol. Furthermore, it also can be produced by carrying out a step of protecting the primary hydroxyl groups of the alcohol compound. In a compound in which primary hydroxyl groups of the alcohol compound are protected beforehand, it is preferable that a part of hydroxyl groups other than the primary hydroxyl groups be protected while a plurality of hydroxyl groups are allowed to remain. In this manner, a structure having at least three hydroxyl groups is obtained easily.

The step of protecting the primary hydroxyl groups of the alcohol compound can be carried out by performing a known reaction for introducing protecting groups.

It is advantageous to select a group that is introduced preferentially into a primary hydroxyl group, as a protecting group for the primary hydroxyl groups of the alcohol compound. Furthermore, for the protecting group, it is advantageous to select one that tends not to undergo a deprotection reaction during the esterification reaction and tends not to allow the ester bond to be cleaved during the deprotection reaction. From these viewpoints, protecting groups that are used preferably are ether protecting groups, silyl ether protecting groups, and acetal protecting groups. Ether protecting groups that are used more preferably are a 1-ethoxyethyl ether group and triphenylmethyl ether group. Silyl ether protecting groups that are used more preferably are a triisopropylsilyl ether group, t-butyldimethylsilyl ether group, and t-butyldiphenylsilyl ether group. Each of these protecting groups can be introduced preferentially into a primary hydroxyl group and can be deprotected under a mild acidic condition, and therefore it has an advantage that deprotection can be achieved without cleaving the ester bond. On the other hand, acetal protecting groups that are used more preferably are an isopropylidene group, cycloheptylidene group, benzylidene group, and p-methoxybenzylidene group. When using an acetal protecting group, it not only can be introduced preferentially into a primary hydroxyl group but also can protect two or more hydroxyl groups including the primary hydroxyl group at the same time. Accordingly, the acetal protecting group is especially suitable for synthesis of the polymerizable monomer (A). Therefore, among the ether protecting groups, silyl ether protecting groups, and acetal protecting groups, the acetal protecting groups are used further preferably. Moreover, from the viewpoints that deprotection is possible under a particularly mild acidic condition and a byproduct produced at the time of deprotection can be removed easily, an isopropylidene group is used particularly preferably.

The step of esterifying a compound in which primary hydroxyl groups of the alcohol compound are protected beforehand and a carboxylic acid having a polymerizable group or a derivative thereof can be carried out according to a known method. For the esterification reaction, it is important to select suitable reaction conditions (particularly, the temperature condition and the type of catalyst) under which a deprotection reaction tends not to occur, with consideration given to the type of the protecting group. Furthermore, it is important to select the reaction conditions (particularly, the amounts of the compound in which primary hydroxyl groups of the alcohol compound are protected beforehand and the carboxylic acid having a polymerizable group or a derivative thereof to be used) so that after the esterification reaction, a plurality of ester bonds are formed and the total number of the protected hydroxyl groups and unreacted hydroxyl groups is at least three, in one molecule.

The step of deprotecting the protecting groups of the primary hydroxyl groups of the resultant ester compound may be carried out according to a known method depending on the type of the protecting group. In this case, it is important to select reaction conditions (particularly, the temperature condition and the type of catalyst) under which the ester bond tends not to be cleaved. As described above, when the ether protecting groups, silyl ether protecting groups, and acetal protecting groups that are preferable as the protecting group of the primary hydroxyl group are used, all of them can be deprotected under mild acidic conditions and therefore deprotection can be performed without allowing the ester bond to be cleaved. Furthermore, the silyl ether protecting groups can be deprotected with extremely high selectivity by the use of a fluorine-containing compound such as TBAF (tetrabutylammonium fluoride) and thus are highly useful. In the case of deprotection under an acidic condition, for example, mineral acids such as hydrochloric acid and sulfuric acid and aqueous solutions thereof; organic acids such as formic acid, acetic acid, and trifluoroacetic acid and aqueous solutions thereof; and cation exchange resin are used preferably. Among these, since the acidity is suitable and deprotection can be performed with cleavage of the ester bond being prevented efficiently, organic acids such as formic acid, acetic acid, and trifluoroacetic acid and aqueous solutions thereof are more preferable, and formic acid, acetic acid, and aqueous solutions thereof are further preferable.

Since the polymerizable monomer (A) has a plurality of polymerizable groups and a plurality of hydroxyl groups, it is excellent in crosslinking reactivity and can interact strongly with a compound having a hydrophilic group. Accordingly, when the polymerizable monomer is mixed with a suitable component into a composition, the composition thus obtained exhibits excellent curability and adhesive properties in various applications including dental applications. From the viewpoint of obtaining both curability and adhesive properties to a tooth structure of the composition in a balanced manner, compounds represented by the aforementioned formulae (6) and (7) can be used in combination.

The amount of polymerizable monomer (A) to be added may be determined appropriately according to the application of the composition. Preferably, 1 to 98 parts by weight of polymerizable monomer (A) is contained in 100 parts by weight of the whole amount of polymerizable monomer components (other polymerizable monomer components will be described later). When a composition in which the amount of the polymerizable monomer (A) to be added is in such a range is used as a dental composition, there are advantages that penetrability into a collagen layer of dentin is excellent and bond strength is high. When the amount of polymerizable monomer (A) to be added is less than 1 part by weight, bond strength may be reduced and bond durability also may be reduced. Therefore, the amount is more preferably at least 2 parts by weight and further preferably at least 5 parts by weight. On the other hand, the amount of polymerizable monomer (A) to be added exceeding 98 parts by weight results in insufficient decalcification and sufficiently high bond strength may not be obtained. Therefore the amount is more preferably 96 parts by weight or less and further preferably 94 parts by weight or less.

Polymerizable monomer (B) having one polymerizable group and at least one hydroxyl group The composition of the present invention is characterized by containing a polymerizable monomer (B) having one polymerizable group and at least one hydroxyl group. Since the composition of the present invention contains a polymerizable monomer (B) in addition to the polymerizable monomer (A), when it is used as a dental composition, it exhibits both excellent bond strength and excellent bond durability. Since the polymerizable monomer (B) used in the present invention has a polymerizable group, not only radical polymerization can occur but also copolymerization with another monomer can occur. From the viewpoint of ease of radical polymerization, the polymerizable group is preferably a (meth)acrylic group or (meth)acrylamide group. The polymerizable monomer (B) is used preferably as a component of a dental composition. However, since the inside of an oral cavity has a humid environment, the polymerizable group may be detached by, for example, hydrolysis. When consideration is given to stimulativeness of a detached polymerizable group to a biological body, the polymerizable group is preferably a methacrylic group or methacrylamide group.

The polymerizable monomer (B) has at least one hydroxyl group and therefore has excellent hydrophilicity, and it is a monofunctional polymerizable monomer, as described above. Accordingly, when the composition of the present invention containing the polymerizable monomer (A) and the polymerizable monomer (B) is used as a dental composition, it has more excellent penetrability into a collagen layer of dentin than a composition containing the polymerizable monomer (A) alone. In the case of a composition containing the polymerizable monomer (B) alone, since the polymerizable monomer (B) has low polymerizability and an unreacted polymerizable monomer (B) remains, the bond strength may be reduced. Accordingly, as with the case of the present invention, it is important to use in combination the polymerizable monomer (A) that is a bifunctional polymerizable monomer and that has at least two hydroxyl groups and the polymerizable monomer (B) that is a monofunctional polymerizable monomer and that has at least one hydroxyl group. By doing so, the unreacted polymerizable monomer (B) and the polymerizable monomer (A) react with each other, which makes it possible not only to increase the bond strength but also to increase the bond durability to the adhesive interface or adhesive layer. Furthermore, when the bond strength is increased, the amount of the dental composition to be used can be reduced.

The polymerizable monomers (B) used in the present invention can be used independently or two or more of them can be used in suitable combination. The polymerizable monomers (B) are not particularly limited, and those represented by the following formula (8) are used suitably.

[Chemical Formula 19]

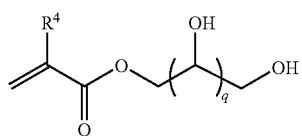

(8)

where $R^4$ indicates a hydrogen atom or an aliphatic hydrocarbon group having 1 to 10 carbon atoms and q denotes an integer of 0 or more.

In the above formula (8), $R^4$ indicates a hydrogen atom or an aliphatic hydrocarbon group having 1 to 10 carbon atoms. For this aliphatic hydrocarbon group having 1 to 10 carbon atoms, groups exemplified as the aliphatic hydrocarbon groups having 1 to 10 carbon atoms for the above $R^1$, $R^2$, and $R^3$ can also be used. In the above formula (8), it is preferable that $R^4$ be a hydrogen atom or methyl group. In this case, there is an advantage of excellent polymerizability.

In the above formula (8), q is an integer of 0 or more, which allows the polymerizable monomer (B) to have at least one hydroxyl group. q is preferably an integer of 0 to 4. This is because when a decomposition product is produced by an action such as hydrolysis inside an oral cavity, the decomposition product is a highly safe compound such as ethylene glycol, glycerol, erythritol, xylitol, sorbitol, or mannitol. q is more preferably 0. This is because when the polymerizable monomer (B) is used in a dental composition, it has excellent penetrability into a collagen layer of dentin and exhibits an excellent effect of combination use with the polymerizable monomer (A). Therefore, it is more preferable that q be 0. In the above formula (8), the decomposition product is ethylene glycol when q is 0, glycerol when q is 1, erythritol when q is 2, xylitol when q is 3, and sorbitol or mannitol when q is 4.

The amount of the polymerizable monomer (B) to be added in the present invention is not particularly limited, but it is preferable that 2 to 5000 parts by weight of polymerizable monomer (B) be contained in 100 parts by weight of polymerizable monomer (A). When a composition in which the amount of the polymerizable monomer (B) to be added is in such a range is used as a dental composition, there are advantages that penetrability into a collagen layer of dentin is excellent and bond strength is high. When the amount of polymerizable monomer (B) to be added is less than 2 part by weight, bond strength may be reduced and bond durability also may be reduced. Therefore, the amount is more preferably at least 5 parts by weight and further preferably at least 10 parts by weight. On the other hand, when the amount of polymerizable monomer (B) to be added exceeds 5000 parts by weight, sufficiently high curability may not be obtained and bond strength may be reduced. Therefore, the amount is more preferably 3000 parts by weight or less and further preferably 2000 parts by weight or less.

Next, arbitrary components of the composition according to the present invention are described. The composition of the present invention may contain components other than the polymerizable monomer (A) and the polymerizable monomer (B) depending on the application of the composition. For instance, the composition of the present invention may contain, as a polymerizable monomer component other than the polymerizable monomer (A) and the polymerizable monomer (B), polymerizable monomer components such as a polymerizable monomer (C) having an acidic group, and a crosslinkable polymerizable monomer (D). Preferably, the polymerizable groups included in these polymerizable monomers are groups that are radical-copolymerizable with polymerizable groups of the polymerizable monomers (A) and (B).

Furthermore, the composition of the present invention may contain a solvent (E), a polymerization initiator (F), a polymerization accelerator (G), and a filler (H).

In the present invention, the phrase "the whole amount of polymerizable monomer components" denotes the total amount of the polymerizable monomers (A) to (D).

Polymerizable Monomer (C) Having Acidic Group

Preferably, the composition of the present invention contains 1 to 90 parts by weight of polymerizable monomer (C) having an acidic group in 100 parts by weight of the whole amount of polymerizable monomer components. When a composition in which the amount of polymerizable monomer (C) having an acidic group to be added is in such a range is used as a dental composition, it has advantages that, for example, pretreatments such as an acid etching treatment and a primer treatment are not necessary, since the polymerizable monomer (C) itself that has an acidic group has an acid-etching effect and a primer treatment effect. Accordingly, a combination with a polymerizable monomer (C) having an acidic group makes it possible to provide a bonding material that is simple to use and has high bond strength and excellent bond durability, particularly preferably a one-component bonding material. When the amount of polymerizable monomer (C) having an acidic group to be added is less than 1 part by weight, the acid-etching effect or primer treatment effect may not be obtained. Therefore, the amount is more preferably at least 2 parts by weight and further preferably at least 5 parts by weight. On the other hand, when the amount of polymerizable monomer (C) having an acidic group to be added exceeds 90 parts by weight, sufficiently high curability may not be obtained and therefore the adhesive properties may be deteriorated. Accordingly, the amount is more preferably 80 parts by weight or less and further preferably 70 parts by weight or less.

Polymerizable monomers (C) having acidic groups can be used independently or two or more of them can be used in suitable combination. The polymerizable monomers (C) having acidic groups are not particularly limited. Examples thereof include a monofunctional polymerizable monomer having one carboxyl group or an acid anhydride group thereof in the molecule, a monofunctional polymerizable monomer having a plurality of carboxyl groups or an acid anhydride group thereof in the molecule, and a monofunctional polymerizable monomer having a phosphinyloxy group or phosphonooxy group in the molecule (also referred to as a monofunctional radical polymerizable phosphoric acid ester).

Examples of the monofunctional polymerizable monomer having one carboxyl group or an acid anhydride group thereof in the molecule include (meth)acrylic acid, N-(meth)acryloylglycine, N-(meth)acryloylaspartic acid, N-(meth)acryloyl-5-aminosalicylic acid, 2-(meth)acryloyloxyethyl hydrogen succinate, 2-(meth)acryloyloxyethyl hydrogen phthalate, 2-(meth)acryloyloxyethyl hydrogen malate, 6-(meth)acryloyloxyethyl naphthalene-1,2,6-tricarboxylic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-4-aminosalicylic acid, and compounds obtained by converting the carboxyl group of these compounds into an acid anhydride group.

Examples of the monofunctional polymerizable monomer having a plurality of carboxyl groups or an acid anhydride group thereof in the molecule include 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)propyl succinate, 4-(2-(meth)acryloyloxyethyl)trimeritate anhydride, 4-(2-(meth)acryloyloxyethyl)trimeritate, 4-(meth)acryloyloxyethyl trimeritate, 4-(meth)acryloyloxybutyl trimeritate, 4-(meth)acryloyloxyhexyl trimeritate, 4-(meth)acryloyloxydecyl trimeritate, 4-(meth)acryloyloxybutyl trimeritate, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, 4-(meth)acryloyloxyethylnaphthalene-1,8-tricarboxylic acid anhydride, 9-(meth)acryloyloxynonane-1,1-dicarboxylic acid, 13-(meth)acryloyloxytridecane-1,1-dicarboxylic acid, and 11-(meth)acrylamideundecane-1,1-dicarboxylic acid.

Examples of the monofunctional polymerizable monomer having a phosphinyloxy group or phosphonooxy group in the molecule (also referred to as a monofunctional radical polymerizable phosphoric acid ester) include 2-(meth)acryloyloxyethyl dihydrogenphosphate, 2-(meth)acryloyloxyethylphenyl hydrogenphosphate, 10-(meth)acryloyloxydecyl dihydrogenphosphate, 6-(meth)acryloyloxyhexyl dihydrogenphosphate, 2-(meth)acryloyloxyethyl-2-bromoethyl hydrogenphosphate, and 2-(meth)acrylamideethyl dihydrogenphosphate.

Examples of other monofunctional polymerizable monomer having an acidic group include a monofunctional polymerizable monomer having a sulfo group in the molecule such as 2-(meth)acrylamide-2-methylpropanesulfonic acid and 10-sulfodecyl(meth)acrylate.

Crosslinkable Polymerizable Monomer (D)

Preferably, the composition of the present invention contains 1 to 90 parts by weight of crosslinkable polymerizable monomer (D) in 100 parts by weight of the whole amount of polymerizable monomer components. When a composition in which the amount of the crosslinkable polymerizable monomer (D) to be added is in such a range is used as a dental composition, it has advantages such as a further improvement in bond strength. When the amount of crosslinkable polymerizable monomer (D) to be added is less than 1 part by weight, sufficiently high bond strength may not be obtained. Therefore, the amount is more preferably at least 2 parts by weight and further preferably at least 5 parts by weight. On the other hand, when the amount of crosslinkable polymerizable monomer (D) to be added exceeds 90 parts by weight, the composition may not penetrate sufficiently into a collagen layer of dentin and thereby high bond strength may not be obtained. Therefore, the amount is more preferably 85 parts by weight or less and further preferably 80 parts by weight or less.

Crosslinkable polymerizable monomers (D) can be used independently or two or more of them can be used in suitable combination. The crosslinkable polymerizable monomers (D) are not particularly limited. Examples thereof include an aromatic compound-based bifunctional polymerizable monomer, an aliphatic compound-based bifunctional polymerizable monomer, and trifunctional or higher polymerizable monomers.

Examples of the aromatic compound-based bifunctional polymerizable monomer include 2,2-bis((meth)acryloyloxyphenyl)propane, 2,2-bis[4-(3-(meth)acryloyloxy)-2-hydroxypropoxyphenyl]propane (commonly known as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)-propane, 2-(4-(meth)acryloyloxydiethoxyphenyl)-2-(4-(meth)acryloyloxytriethoxy-phenyl)propane, 2-(4-(meth)acryloyloxydipropoxyphenyl)-2-(4-(meth)acryloyloxytriethoxy-phenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromeritate.

Examples of the aliphatic compound-based bifunctional polymerizable monomer include ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, and 2,2,4-trimethylhexamethylenebis(2-carbamoyloxyethyl)dimethacrylate (commonly known as "UDMA").

Examples of the trifunctional or higher polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, dipentaerythritol hexa(meth)acrylate, N,N-(2,2,4-trimethylhexamethylene)bis[2-(aminocarboxy)propane-1,3-diol] tetramethacrylate, and 1,7-diacryloyloxy-2,2,6,6-tetraacryloyloxymethyl-4-oxyheptane.

The composition of the present invention may contain a polymerizable monomer other than the aforementioned (A), (B), (C), and (D) as required.

Solvent (E)

Preferably, the composition of the present invention contains a solvent (E) depending on the specific embodiment. Organic solvents (E) can be used independently or two or more of them can be used in suitable combination. Examples of the organic solvent (E) include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Particularly, when both safety to biological bodies and easy removal based on volatility are taken into consideration, the organic solvent (E) is preferably a water-soluble organic solvent. Specifically, at least one selected from the group consisting of ethanol, 2-propanol, 2-methyl-2-propanol, acetone, and tetrahydrofuran can be used preferably. In a particularly preferred embodiment, the solvent (E) contains water. When the composition containing water is used as a dental composition, it has advantages that, for example, it exhibits both excellent bond strength and excellent bond durability. Preferably, water is free of impurities that have adverse effects, and distilled water or ion exchanged water is preferable. The water may be used independently, or it may be used in the form of a mixed solvent of water and a solvent other than water.

The amount of solvent (E) to be added is not particularly limited and the solvent (E) may not need to be added depending on the embodiment. In an embodiment using the solvent (E), it is preferable that 1 to 2000 parts by weight of solvent (E) be contained with respect to 100 parts by weight of the whole amount of polymerizable monomer components. The preferable amount of the solvent (E) to be added varies considerably depending on the embodiment in which it is used. Therefore, preferable amounts of solvents (E) to be added according to respective embodiments are indicated together with description of specific embodiments of the composition of the present invention described later.

Polymerization Initiator (F)

A polymerization initiator (F) used in the present invention can be selected from polymerization initiators commonly used in the industrial field. Among them, polymerization initiators used for dental applications are used preferably. Particularly, photopolymerization initiators and chemical polymerization initiators are used independently or two or more of them are used in suitable combination.

Examples of the photopolymerization initiator include (bis)acylphosphine oxides, water-soluble acylphosphine oxides, thioxanthones or the quaternary ammonium salts of thioxanthones, ketals, alpha-diketones, coumarins, anthraquinones, benzoin alkyl ether compounds, and alpha-amino ketone compounds.

Among (bis)acylphosphine oxides used as the photopolymerization initiator, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl) phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

Preferably, the water-soluble acylphosphine oxides used as the photopolymerization initiator have alkali metal ions, alkaline earth metal ions, pyridinium ions, or ammonium ions in the acylphosphine oxide molecules. For instance, the water-soluble acylphosphine oxides can be synthesized by the method disclosed in EP 0009348 or JP 57 (1982)-197289 A.

Specific examples of the aforementioned water-soluble acylphosphine oxides include sodium monomethylacetylphosphonate, sodium monomethyl(1-oxopropyl) phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium monomethylacetylphosphonate, sodium acetylmethylphosphonate, methyl-4-(hydroxymethoxyphosphinyl)-4-oxobutanoate sodium salt, methyl-4-oxophosphonobutanoate monosodium salt, acetylphenylphosphinate sodium salt, sodium (1-oxopropyl) pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl) phosphinate sodium salt, methyl(2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl)methylphosphonite sodium salt, methyl(2-methyloxathiolane-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl) methylphosphinate sodium salt, (1-ethylthiovinyl) methylphosphinate sodium salt, methyl(2-methylperhydro-1,3-diazin-2-yl)phosphinate sodium salt, methyl(2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxime sodium salt, 1-[(N-ethoxyimino)ethyl]methylphosphinate sodium salt, methyl(1-phenyliminoethyl)phosphinate sodium salt, methyl (1-phenylhydrazone ethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methyl phosphinate sodium salt, formylmethylphosphinate sodium salt, (1,1-dimethoxypropyl)methylphosphinate sodium salt, methyl(1-oxopropyl)phosphinate sodium salt, dodecylguanidine salt of (1,1-dimethoxypropyl)methylphosphinate, isopropylamine salt of (1,1-dimethoxypropyl)methylphosphinate, acetylmethylphosphinate thiosemicarbazone sodium salt, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and ammonium salt of 2,4,6-trimethylbenzoylphenylphosphine oxide. Furthermore, examples thereof also include compounds described in JP 2000-159621 A.

Among these (bis)acylphosphine oxides and water-soluble acylphosphine oxides, particularly preferable ones are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of thioxanthones or the quaternary ammonium salts of thioxanthones that are used as the above-mentioned photopolymerization initiators include thioxanthone, 2-chlorothioxanthen-9-one, 2-hydroxy-3-(9-oxy-9H-thioxanthen-4-yloxy)-N,N, N-trimethyl-propaneaminium chloride, 2-hydroxy-3-(1-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N, N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N, N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among the thioxanthones or the quaternary ammonium salts of thioxanthones, a particularly preferable thioxanthone is 2-chlorothioxanthen-9-one, and a particularly preferable quaternary ammonium salt of thioxanthone is 2-hydroxy-3-(3,4-dimethyl-9H-thioxanthen-2-yloxy)-N,N, N-trimethyl-1-propaneaminium chloride.

Examples of ketals used as the photopolymerization initiator include benzyl dimethyl ketal and benzyl diethyl ketal.

Examples of the alpha-diketones used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

Examples of the coumarin compound used as the aforementioned photopolymerization initiator include compounds described in JP 9 (1997)-3109 A and JP 10 (1998)-245525 A such as 3,3'-carbonylbis(7-diethylamino)coumarin, 3-(4-methoxybenzoyl)coumarin, 3-thienoyl coumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazole-2-ilidene)acetyl]coumarin, 3-[(1-methylnaphtho[1,2-d]thiazole-2-ilidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-1,1,7,7-tetramethyl1H, 5H, 11H-[1]benzopyrano[6,7,8-ij]quinolizine-11-one, and 10-(2-benzothiazoyl)-2,3,6,7-tetrahydro-1,1,7,7-tetramethyl1H, 5H, 11H-[1]-benzopyrano[6,7,8-ij]quinolizin-11-one.

Among the above-mentioned coumarin compounds, particularly 3,3'-carbonylbis(7-diethylaminocoumarin) and 3,3'-carbonylbis(7-dibutylaminocoumarin) are suitable.

Examples of the anthraquinones used as the aforementioned photopolymerization initiator include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers used as the aforementioned photopolymerization initiator include benzoin methyl ether, benzoin ethyl ether, benzoin isopropyl ether, and benzoin isobutyl ether.

Examples of the alpha-aminoketones used as the aforementioned photopolymerization initiator include 2-methyl-1-[4-(methylthio)phenyl]-2-morpholinopropan-1-one.

Preferably, among these photopolymerization initiators, at least one selected from the group consisting of (bis)acylphosphine oxides, salts thereof, alpha-diketones, and coumarin compounds is used. This makes it possible to obtain a composition that has excellent photocurability in visible and near-ultraviolet ranges and sufficiently high photocurability regardless of which light source among a halogen lamp, light-emitting diode (LED), and xenon lamp is used.

Among the polymerization initiators (F) used in the present invention, a chemical polymerization initiator that is used preferably is organic peroxide. The organic peroxide used as the chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate.

Examples of ketone peroxide used as the chemical polymerization initiator include methyl ethyl ketone peroxide, methyl isobutyl ketone peroxide, methylcyclohexanone peroxide, and cyclohexanone peroxide.

Examples of hydroperoxide used as the chemical polymerization initiator include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of dialkyl peroxide used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of peroxyketal used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of peroxyester used as the chemical polymerization initiator include alpha-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethyl hexanoate, t-butylperoxy acetate, t-butylperoxy benzoate, and t-butylperoxymaleic acid.

Examples of peroxydicarbonate used as the chemical polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxide is used preferably from the viewpoint of a comprehensive balance of safety, storage stability, and radical production ability, and among these, benzoyl peroxide is used particularly preferably.

The amount of polymerization initiator (F) to be added in the present invention is not particularly limited. However, from the viewpoint of, for example, curability of the resultant composition, it is preferable that 0.001 to 30 parts by weight of polymerization initiator (F) be contained with respect to 100 parts by weight of the whole amount of polymerizable monomer components. When the amount of polymerization initiator (F) to be added is less than 0.001 part by weight, polymerization may not proceed sufficiently and thereby bond strength may be reduced. Therefore, the amount is more preferably at least 0.05 part by weight. On the other hand, when the amount of polymerization initiator (F) to be added exceeds 30 parts by weight, in the case where the polymerization initiator itself has low polymerization performance, sufficiently high bond strength may not be obtained and further precipitation from the composition may occur. Therefore, the amount is more preferably 20 parts by weight or less.

Polymerization Accelerator (G)

In an preferred embodiment, a polymerization accelerator (G) is used. Examples of the polymerization accelerator (G) used in the present invention include amines, sulfinic acids and salts thereof, borate compounds, barbituric acid derivatives, triazine compounds, copper compounds, tin compounds, vanadium compounds, halogen compounds, aldehydes, thiol compounds, sulfite, bisulfite, and thiourea compounds.

Amines used as the polymerization accelerator (G) can be divided into aliphatic amines and aromatic amines. Examples of aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of curability and storage stability of the composition, and particularly, N-methyldiethanolamine and triethanolamine are used more preferably.

Examples of aromatic amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably from the viewpoint of being capable of providing the composition with excellent curability.

Examples of sulfinic acid and salt thereof used as the polymerization accelerator (G) include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are particularly preferable.

The borate compound used as the polymerization accelerator (G) is preferably an arylborate compound. Specific examples of arylborate compounds that are used preferably include, as a borate compound having one aryl group in one molecule, sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of trialkylphenylboron, trialkyl(p-chlorophenyl)boron, trialkyl(p-fluorophenyl)boron, trialkyl(3,5-bistrifluoromethyl)phenylboron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (each alkyl group is at least one selected from the group consisting of, for example, an n-butyl group, an n-octyl group, and an n-dodecyl group).

Examples of the borate compound having two aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of dialkyldiphenylboron, dialkyldi(p-chlorophenyl)boron, dialkyldi(p-fluorophenyl)boron, dialkyldi(3,5-bistrifluoromethyl)phenylboron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (each alkyl group is at least one selected from the group consisting of, for example, an n-butyl group, an n-octyl group, and an n-dodecyl group).

Examples of the borate compound having three aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of monoalkyltriphenylboron, monoalkyltri(p-chlorophenyl)boron, monoalkyltri(p-fluorophenyl)boron, monoalkyltri(3,5-bistrifluoromethyl)phenylboron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl) boron (each alkyl group is one selected from, for example, an n-butyl group, an n-octyl group, and an n-dodecyl group).

Furthermore, examples of the borate compound having four aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, (3,5-bistrifluoromethyl)phenyltriphenylboron, (p-nitrophenyl)triphenylboron, (m-butyloxyphenyl)triphenylboron, (p-butyloxyphenyl)triphenylboron, (m-octyloxyphenyl)triphenylboron, and (p-octyloxyphenyl)triphenylboron.

More preferably, from the viewpoint of storage stability, among these arylborate compounds, a borate compound having three or four aryl groups in one molecule is used. Furthermore, one of these arylborate compounds can be used or two or more of them can be used in mixture.

Examples of a barbituric acid derivative used as the polymerization accelerator (G) include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids, as well as salts thereof (particularly, alkali metals or alkaline earth metals are preferable). Examples of salts of these barbituric acids include sodium 5-butylbarbiturate, sodium 1,3,5-trimethylbarbiturate, and sodium 1-cyclohexyl-5-ethylbarbiturate.

Examples of particularly preferable barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids.

Examples of the triazine compound used as the polymerization accelerator (G) include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-(α,α,β-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Particularly preferable ones among the triazine compounds described above as examples are 2,4,6-tris(trichloromethyl)-s-triazine in terms of polymerization activity and 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine in terms of storage stability. One of the above-mentioned triazine compounds may be used or two or more of them may be used in mixture.

Examples of the copper compound used preferably as the polymerization accelerator (G) include copper acetylacetonate, copper (II) acetate, copper oleate, copper (II) chloride, and copper (II) bromide.

Examples of the tin compound used as the polymerization accelerator (G) include di-n-butyltin dimalate, di-n-octyltin dimalate, di-n-octyltin dilaurate, and di-n-butyltin dilaurate. Particularly preferable tin compounds are di-n-octyltin dilaurate and di-n-butyltin dilaurate.

The vanadium compound used as the polymerization accelerator (G) is preferably one of tetravalent and/or pentavalent vanadium compounds. Examples of the tetravalent and/or pentavalent vanadium compounds include compounds described in JP 2003-96122 A such as divanadium (IV) tetroxide, vanadyl (IV) acetylacetonate, vanadyl (IV) oxalate, vanadyl (IV) sulfate, oxobis(1-phenyl-1,3-butanedionate)vanadium (IV), bis(maltolato)oxovanadium (IV), vanadium (V) pentoxide, sodium metavanadate (V), and ammonium metavanadate (V).

Examples of the halogen compound used preferably as the polymerization accelerator (G) include dilauryldimethylammoniumchloride, lauryldimethylbenzylammoniumchloride, benzyltrimethylammoniumchloride, tetramethylammoniumchloride, benzyldimethylcetylammoniumchloride, and dilauryldimethylammoniumbromide.

Examples of aldehydes used as the polymerization accelerator (G) include terephthalaldehyde and a benzaldehyde derivative. Examples of the benzaldehyde derivative include dimethylaminobenzaldehyde, p-methyloxybenzaldehyde, p-ethyloxybenzaldehyde, and p-n-octyloxybenzaldehyde. Among these, from the viewpoint of curability, p-n-octyloxybenzaldehyde is used preferably.

Examples of the thiol compound used as the polymerization accelerator (G) include 3-mercaptopropyltrimethoxysilane, 2-mercaptobenzooxazol, decanethiol, and thiobenzoic acid.

Examples of sulfite used as the polymerization accelerator (G) include sodium sulfite, potassium sulfite, calcium sulfite, and ammonium sulfite.

Examples of bisulfate used as the polymerization accelerator (G) include sodium bisulfate and potassium bisulfate.

Examples of the thiourea compound used as the polymerization accelerator (G) include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

The amount of polymerization accelerator (G) to be added in the present invention is not particularly limited. However, from the viewpoints of, for example, curability of the resultant composition, it is preferable that 0.001 to 30 parts by weight of polymerization accelerator (G) be contained with respect to 100 parts by weight of the whole amount of polymerizable monomer components. When the amount of polymerization accelerator (G) to be added is less than 0.001 part by weight, polymerization may not proceed sufficiently and bond strength may be reduced. Therefore, the amount is more preferably at least 0.05 part by weight. On the other hand, when the amount of polymerization accelerator (G) to be added exceeds 30 parts by weight, in the case where the polymerization initiator itself has low polymerization performance, sufficiently high bond strength may not be obtained and further precipitation from the composition may occur. Therefore, the amount is more preferably 20 parts by weight or less.

Filler (H)

Preferably, a filler (H) further is mixed into a composition of the present invention depending on the embodiment. Generally, such fillers are divided roughly into organic fillers, inorganic fillers, and organic-inorganic composite fillers. Examples of materials for the organic fillers include polymethylmethacrylate, polyethylmethacrylate, a methylmethacrylate-ethylmethacrylate copolymer, cross-linked polymethylmethacrylate, cross-linked polyethylmethacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used independently or a mixture of two or more of them may be used. The shapes of the organic fillers are not particularly limited, and particle sizes of the fillers to be used can be selected appropriately. From the viewpoints of, for example, handling ability and mechanical strength of the resultant composition, the mean particle size of the organic fillers is preferably 0.001 to 50 µm and more preferably 0.001 to 10 µm.

Examples of materials for the inorganic fillers include quartz, silica, alumina, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. Similarly, these can be used independently or two or more of them can be used in mixture. The shapes of the inorganic fillers are not particularly limited and particle sizes of the fillers to be used can be selected appropriately. From the viewpoints of, for example, handling ability and mechanical strength of the resultant composition, the mean particle size of the inorganic fillers is preferably 0.001 to 50 µm and more preferably 0.001 to 10 µm.

Examples of the shapes of the inorganic fillers include amorphous fillers and spherical fillers. From the viewpoint of improving the mechanical strength of a composition, it is preferable that spherical fillers be used as the inorganic fillers. Furthermore, in the case of using the spherical fillers, when a composition of the present invention is used as a dental composite resin, there also is an advantage that a composition resin with excellent surface smoothness is obtained. In this case, the spherical fillers are fillers in which when a photograph thereof is taken with a scanning electron microscope (hereinafter abbreviated as SEM), particles observed within a unit field of view are rounded and the mean uniformity obtained by dividing the particle size in the direction orthogonal to the maximum diameter by the maximum diameter is at least 0.6. The mean particle size of the spherical fillers is preferably 0.1 to 5 µm. When the mean particle size is less than 0.1 µm, the filling rate of the spherical fillers in the composition decreases and thereby the mechanical strength may be reduced. On the other hand, when the mean particle size exceeds 5 µm, the surface areas of the spherical fillers are reduced and a cured body with high mechanical strength may not be obtained.

The inorganic fillers may be used after the surfaces thereof are treated beforehand with a known surface-treating agent such as a silane coupling agent in order to adjust fluidity of the composition as required. Examples of such a surface-treating agent include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite fillers used in the present invention can be obtained as follows. That is, a monomer compound is added to the aforementioned inorganic filler beforehand, this is made into a paste and is then polymerized, and thereafter this is crushed. The organic-inorganic composite filler that can be used is, for example, a TMPT filler (obtained by mixing trimethylolpropane methacrylate with a silica filler, polymerizing it, and then crushing it). The shape of the organic-inorganic composite filler is not particularly limited, and the particle size of the filler to be used can be selected appropriately. From the viewpoints of, for example, handling ability and mechanical strength of the resultant composition, the mean particle size of the organic-inorganic composite filler is preferably 0.001 to 50 µm and more preferably 0.001 to 10 µm.

The amount of the filler (H) to be added in the present invention is not particularly limited, but it is preferable that 1 to 2000 parts by weight of filler (H) be contained with respect to 100 parts by weight of the whole amount of polymerizable monomer components. The preferable amount of filler (H) to be added varies considerably depending on the embodiment to be employed. Accordingly, preferable amounts of the filler (H) to be added according to the respective embodiments are indicated together with description of specific embodiments of the composition of the present invention described later.

In addition, for example, a pH adjuster, polymerization inhibitor, ultraviolet absorbent, thickening agent, colorant, antibacterial agent, and flavor may be added to the composition of the present invention within a range that does not inhibit the effect of the present invention.

The composition of the present invention contains: the polymerizable monomer (A) having a plurality of polymerizable groups and a plurality of hydroxyl groups; and the polymerizable monomer (B) having one polymerizable group and at least one hydroxyl groups. Accordingly, when these polymerizable monomers are mixed with a suitable component into a composition as required, the composition thus obtained exhibits excellent curability and adhesive properties in various applications including dental applications. Particularly, since the composition of the present invention has high penetrability into a collagen layer of dentin as well as high bond strength and bond durability to a tooth structure (particularly dentin), it can be used suitably as a dental composition. This dental composition can be used for dental materials such as a primer, bonding material, composite resin, cement (resin cement, glass ionomer cement, and resin-reinforced glass ionomer cement), pit and fissure sealant, and denture base resin. Particularly, a dental composition composed of the composition of the present invention can be used suitably as a primer, bonding material, composite resin, or cement. In this case, the composition may be used as a two component type in which the components of the composition are divided into two. Hereinafter, respective embodiments will be described in detail.

As described above, when a lost part of a tooth is filled or covered with a restorative material, a dental adhesive is used generally. Typically, the dental adhesive is allowed to act on dentin. In this case, when such a dental adhesive is allowed to act on dentin, it is important for the dental adhesive to have an decalcifying effect that allows a dentin surface to be dissolved with an acidic component, a penetration effect that allows a monomer component to penetrate into a collagen layer of the dentin, and a curing effect that allows the monomer component thus penetrated to solidify to form a hybrid layer (hereinafter also referred to as a "resin-impregnated layer") with collagen. Generally, a bonding system in which these three steps, "decalcifying", "penetration", and "curing", are performed separately is referred to as a "three-step bonding system". Basically, a product used for the penetration step is a primer, and a product used for the curing step is a bonding material.

Recently, in order to simplify the operation process, a product that allows the decalcifying step and the penetration step to be performed together in one step has been developed and has been used practically. The product is referred to as a "self-etching primer". Generally, the bonding system using a self-etching primer and a bonding material is referred to as a "two-step bonding system". The polymerizable monomer (A) used in the present invention has at least two hydroxyl groups and has high hydrophilicity. Therefore, it easily penetrates into a collagen layer of dentin. The polymerizable monomer (B) also has high penetrability into a collagen layer of dentin. Accordingly, it is preferable that the composition of the present invention be used as a dental primer, and also be used as a dental self-etching primer.

Preferably, the primer using the composition of the present invention is a composition containing a polymerizable monomer (A), polymerizable monomer (B), polymerizable monomer (C) having an acidic group, solvent (E), polymerization initiator (F), and polymerization accelerator (G). More preferably, this composition contains a polymerizable monomer (D) having crosslinkability. The amounts of respective components to be added are preferably 1 to 97 parts by weight of (A), 1 to 90 parts by weight of (C), and 0 to 90 parts by weight of (D), and more preferably 2 to 96 parts by weight of (A), 1 to 80 parts by weight of (C), and 1 to 80 parts by weight of (D), in 100 parts by weight of the whole amount of polymerizable monomer components. The amount of (B) to be added is preferably 2 to 5000 parts by weight, and more preferably 5 to 1000 parts by weight, with respect to 100 parts by weight of (A). The amounts of (E), (F) and (G) to be added are preferably 1 to 2000 parts by weight of (E), 0.001 to 30 parts by weight of (F), and 0.001 to 30 parts by weight of (G), and more preferably 5 to 1500 parts by weight of (E), 0.05 to 20 parts by weight of (F), and 0.05 to 20 parts by weight of (G), with respect to 100 parts by weight of the whole amount of polymerizable monomer components.

In the primer using a composition of the present invention, since the polymerizable monomer (A) has at least two hydroxyl groups in the molecule and the polymerizable monomer (B) used in the present invention has at least one hydroxyl group in the molecule, the composition of the present invention has high hydrophilicity and thereby penetrability into a collagen layer of dentin is improved. Accordingly, amines are preferably used as the polymerization accelerator (G), and the solvent (E) is preferably a water-soluble solvent. A solvent may be used alone as the solvent (E), but preferably the solvent (E) contains water. The content of water in the solvent (E) is preferably at least 10 wt. %, more preferably at least 30 wt. %, further preferably at least 50 wt. %, and most preferably the solvent (E) consist substantially of water alone.

The composition of the present invention is used preferably as a bonding material. Preferably, the bonding material in the aforementioned "two-step bonding system" is a composition containing the aforementioned (A), (B), (F), (G) and (H). More preferably, such a composition further contains (C) and/or (D). The amounts of respective components to be added are preferably 1 to 95 parts by weight of (A), 0 to 90 parts by weight of (C), and 0 to 90 parts by weight of (D), and more preferably 2 to 93 parts by weight of (A), 1 to 80 parts by weight of (C), and 1 to 80 parts by weight of (D), in 100 parts by weight of the whole amount of polymerizable monomer components. As in the case of the above-mentioned (A) used in the present invention, the use of a compound having two polymerizable groups allows a cured product to have increased mechanical strength. From such a viewpoint, it is more preferable that the aforementioned (D) be a polymerizable monomer having at least two polymerizable groups. The amount of (B) to be added is preferably 2 to 5000 parts by weight, and more preferably 5 to 1000 parts by weight, with respect to 100 parts by weight of (A). The amounts of (E), (F), (G) and (H) to be added are preferably 1 to 2000 parts by weight of (E), 0.001 to 30 parts by weight of (F), 0.001 to 30 parts by weight of (G), and 1 to 30 parts by weight of (H), and more preferably 5 to 1500 parts by weight of (E), 0.05 to 20 parts by weight of (F), 0.05 to 20 parts by weight of (G), and 2 to 20 parts by weight of (H), with respect to 100 parts by weight of the whole amount of polymerizable monomer components.

Recently, since there are demands for further simplification in operations, products that allow three steps of "decalcifying", "penetration", and "curing" to be performed together in one step also have been developed and are referred to as "one-step bonding systems". Two typical products of the bonding material used in such a one-step bonding system are a bonding material in which two separate liquids of liquid A and liquid B are mixed together immediately before use and a bonding material that is provided in the form of one liquid from the beginning and that is a so-called one-component one-step bonding system. Among these, the one-component type product further simplifies the process and therefore has a greater advantage in use. When a composition of the present invention is used as the bonding material of the aforementioned one-component one-step bonding system, the composition is preferably a composition containing (A), (B), (C), (E), (F), (G) and (H), and further preferably, such a composition further contains (D). The amounts of respective components to be added are preferably 1 to 95 parts by weight of (A), 1 to 90 parts by weight of (C), and 0 to 90 parts by weight of (D), and more preferably 2 to 94 parts by weight of (A), 2 to 80 parts by weight of (C), and 2 to 80 parts by weight of (D), in 100 parts by weight of the whole amount of polymerizable monomer components. The amount of (B) to be added is preferably 2 to 5000 parts by weight, and more preferably 5 to 1000 parts by weight, with respect to 100 parts by weight of (A). In the one-component one-step bonding system, since the "penetration" and "curing" are performed at one time, the use of a polymerizable monomer having at least two hydroxyl groups and two polymerizable groups like the aforementioned (A) is of great significance. The amounts of (E), (F), (G) and (H) to be added are preferably 1 to 2000 parts by weight of (E), 0.001 to 30 parts by weight of (F), 0.001 to 30 parts by weight of (G), and 1 to 30 parts by weight of (H), and more preferably 5 to 1500 parts by weight of (E), 0.05 to 20 parts by weight of (F), 0.05 to 20 parts by weight of (G), and 2 to 20 parts by weight of (H), with respect to 100 parts by weight of the whole amount of polymerizable monomer components.

The composition of the present invention is used preferably as composite resin. When the composition of the present invention is used as a composite resin, the composition is preferably a composition containing (A), (B), (D), (F), (G) and (H), and such a composition can further contain (C). Generally, the composite resin is used in the form of filling a cavity after the cavity is formed by cutting a site of caries incidence. Thereafter, generally, the composite resin filling the cavity is cured through photopolymerization. Therefore, it is preferable that a photopolymerization initiator be used as the aforementioned (F). Furthermore, since the composite resin that has filled the cavity and that has been cured as described above is subjected to occlusal pressure inside an oral cavity, high mechanical strength is required. Accordingly, the content of the filler (H) in the composition is preferably 30 to 2000 parts by weight and more preferably 50 to 1500 parts by weight, with respect to 100 parts by weight of the whole amount of polymerizable monomer components. When the content of the filler (H) is less than 30 parts by weight, mechanical strength of the cured product may be insufficient. On the other hand, when the content of the filler (H) exceeds 2000 parts by weight, it may become difficult to disperse the filler (H) uniformly throughout the whole amount of polymerizable monomer components, which may result in a composition that is insufficient in mechanical strength and handling ability. The amounts of respective components to be added are preferably 1 to 95 parts by weight of (A), 0 to 50 parts by weight of (C), and 1 to 90 parts by weight of (D), and more preferably 2 to 93 parts by weight of (A), 0 to 30 parts by weight of (C), and 2 to 85 parts by weight of (D), in 100 parts by weight of the whole amount of polymerizable monomer components. The amount of (B) to be added is preferably 2 to 5000 parts by weight, and more preferably 5 to 1000 parts by weight, with respect to 100 parts by weight of (A). The amounts of (F), (G) and (H) to be added are preferably 0.001 to 30 parts by weight of (F), 0.001 to 30 parts by weight of (G), and 30 to 2000 parts by weight of (H), and more preferably 0.05 to 20 parts by weight of (F), 0.05 to 20 parts by weight of (G), and 50 to 1500 parts by weight of (H), with respect to 100 parts by weight of the whole amount of polymerizable monomer components.

Furthermore, the use of a composition of the present invention as a dental cement also is one of preferable embodiments. Examples of preferable cements include a resin cement, glass ionomer cement, and resin-reinforced glass ionomer cement. When the composition of the present invention is used as a resin cement, the composition is preferably one containing (A), (B), (D), (F), (G) and (H). Such a composition further can contain (C). The dental cement is used suitably as, for example, a luting material that is used in fixing a metal or ceramics dental crown restorative material, which is referred to as an "inlay" or "crown", to a tooth. As in the case of the aforementioned (A) used in the present invention, when two polymerizable groups are included, the resultant cured product has increased mechanical strength and can withstand, for example, occlusal pressure. From such a viewpoint, it is more preferable that the aforementioned (D) be a polymerizable monomer having at least two polymerizable groups. Furthermore, in the case of the form of usage as described above, since many of the dental crown restorative materials have optical opacity, it is not easy to cure the cement by only photopolymerization. Therefore, it is preferable that a chemical polymerization initiator be used as the aforementioned (F). Furthermore, when polymerization is performed by using a chemical polymerization initiator, in order to improve the reactivity thereof, the use of amines and/or sulfinic acid and salt thereof as the aforementioned (G) is preferable and the simultaneous use of amines and sulfinic acid and salt thereof is more preferable. The filler (H) used is not particularly limited.

When the cement is intended to be provided with a property of sustained-release of fluoride, it is preferable that at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass be used as the filler (H), and it is more preferable that fluoroaluminosilicate glass and/or barium fluoroaluminosilicate glass be used as the filler (H). On the other hand, when the cement is intended to be provided with radiopacity, it is preferable that at least one selected from the group consisting of barium glass, strontium glass, barium boroaluminosilicate glass, strontium boroaluminosilicate glass, strontium fluoroaluminosilicate glass, and barium fluoroaluminosilicate glass be used as the filler (H), and it is more preferable that barium glass and/or barium fluoroaluminosilicate glass be used as the filler (H).

When a chemical polymerization initiator is used, from the viewpoint of storage stability, it is preferable that the aforementioned (F) and (G) be stored in separate containers, respectively. That is, in a preferred embodiment, the resin cement is used in the form of a two component type. In a more preferred embodiment, the resin cement is used in the form of two paste type. Preferably, the respective pastes are stored while being separated from each other, the two pastes are mixed together immediately before use, and thereby chemical polymerization is allowed to proceed to cure the mixture. The aforementioned pastes each are prepared by mixing a liquid component of, for example, polymerizable monomer with a filler (H) (powder) together. Furthermore, when sulfinic acid and salt thereof are used as the aforementioned (G), from the viewpoint of storage stability, it is preferable that the aforementioned (C) and (G) be stored in separate containers, respectively. Suppose that the aforementioned two pastes are referred to as a paste A and a paste B, respectively, an embodiment in which the paste A contains (A), (B), (C), (F), and (H) and the paste B contains (A), (G), and (H) is used particularly suitably. An embodiment in which the aforementioned paste B contains (B) may be used.

When the composition of the present invention is used as a dental cement, the amounts of respective components to be added are not particularly limited. However, in 100 parts by weight of the whole amount of polymerizable monomer components, the composition contains preferably 1 to 95 parts by weight of (A), 1 to 90 parts by weight of (C), and 1 to 90 parts by weight of (D), and more preferably 2 to 93 parts by weight of (A), 2 to 80 parts by weight of (C), and 2 to 80 parts by weight of (D). The amount of (B) to be added is preferably 2 to 5000 parts by weight, and more preferably 5 to 1000 parts by weight, with respect to 100 parts by weight of (A). When consideration is given to obtaining a suitable setting time, the amounts of the aforementioned (F) and (G) to be added are preferably 0.001 to 30 parts by weight of (F) and 0.001 to 30 parts by weight of (G), and more preferably 0.05 to 20 parts by weight of (F) and 0.05 to 20 parts by weight of (G), with respect to 100 parts by weight of the whole amount of polymerizable monomer components.

Furthermore, with respect to 100 parts by weight of the whole amount of polymerizable monomer components, the content of (H) is preferably 30 to 2000 parts by weight and more preferably 50 to 1500 parts by weight. When the content of the filler (H) is less than 30 parts by weight, mechanical strength of the cured product may be insufficient. On the other hand, in the case where the content of the filler (H) exceeds 2000 parts by weight, when the resin cement is used as a two-paste-type cement, which is a preferred embodiment, the pastes lack fluidity, which makes it difficult to carry out sufficient mixing, and therefore the cured product may have reduced strength.

The composition of the present invention is used preferably as a glass ionomer cement and more preferably as a resin-reinforced glass ionomer cement. The glass ionomer cement is typically one in which an inorganic filler such as fluoroaluminosilicate glass and polyalkenoic acid such as polyacrylic acid are reacted with each other through an acid-base reaction to be cured. Conceivably, the polyacrylic acid interacts with calcium contained in hydroxyapatite composing a tooth structure and thereby a bonding function is exhibited. When a composition of the present invention is used as a glass ionomer cement, particularly preferably as a resin-reinforced glass ionomer cement, the composition is preferably one containing (A), (B), (D), (E), (F), (G), (H) and polyalkenoic acid. Such a composition can further contain (C).

The aforementioned polyalkenoic acid is a polymer of unsaturated monocarboxylic acid or unsaturated dicarboxylic acid. Specific examples of the polyalkenoic acid include homopolymers of, for example, acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, and utraconic acid, or copolymers of these unsaturated carboxylic acids, or copolymers of these unsaturated carboxylic acids and monomers copolymerizable therewith. In the case of the copolymers, the ratio of the unsaturated carboxylic acid unit is preferably at least 50 mol % with respect to the total structure unit. An ethylenically unsaturated polymerizable monomer is preferable as the copolymerizable monomer, and examples thereof include styrene, acrylamide, acrylonitrile, methyl methacrylate, acrylic acid salts, vinyl chloride, allyl chloride, vinyl acetate, and 1,1,6-trimethylhexamethylene dimethacrylate ester. Among those polyalkenoic acids, a homopolymer or copolymer of acrylic acid or maleic acid is preferable. When these polyalkenoic acids have a weight-average molecular weight of less than 5,000, the cured product of the dental cement composition may have reduced strength and poor durability. On the other hand, when it has a weight-average molecular weight exceeding 40,000, it may have high consistency during mixing of the dental cement composition and therefore may have lower operability. Accordingly, a preferable weight-average molecular weight of the polyalkenoic acid is 5,000 to 40,000.

From the viewpoints of curability in the acid-base reaction and the property of sustained-release of fluoride of the composition, the filler (H) to be used is preferably at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass, and more preferably fluoroaluminosilicate glass and/or barium fluoroaluminosilicate glass.

The amount of solvent (E) to be added is not particularly limited, but the solvent (E) is preferably used in the form of a mixed solvent with water. When water is contained in such a form, the acid-base reaction is allowed to proceed smoothly. The content of water in the mixed solvent is preferably at least 50 wt. %, more preferably at least 70 wt. %, and further preferably at least 90 wt. %.

When a composition of the present invention is used as a glass ionomer cement, particularly preferably as a resin-reinforced glass ionomer cement, the amounts of respective components to be added are not particularly limited. However, in 100 parts by weight of the whole amount of polymerizable monomer components, the composition contains preferably 1 to 97 parts by weight of (A), 0 to 50 parts by weight of (C), and 0 to 97 parts by weight of (D), and more preferably 2 to 95 parts by weight of (A), 0 to 30 parts by weight of (C), and 2 to 95 parts by weight of (D). The amount of (B) to be added is preferably 2 to 5000 parts by weight, and more preferably 5 to 1000 parts by weight, with respect to 100 parts by weight of (A). When consideration is given to obtaining a suitable setting time, the amounts of the aforementioned (F) and (G) to be added are preferably 0.001 to 30 parts by weight of (F) and 0.001 to 30 parts by weight of (G), and more preferably 0.05 to 20 parts by weight of (F) and 0.05 to 20 parts by weight of (G), with respect to 100 parts by weight of the whole amount of polymerizable monomer components. Furthermore, with respect to 100 parts by weight of the whole amount of polymerizable monomer components, the content of (H) is preferably 30 to 2000 parts by weight and more preferably 50 to 1500 parts by weight. When the content of the filler (H) is less than 30 parts by weight, mechanical strength of the cured product may be insufficient. On the other hand, when the content of the filler (H) exceeds 2000 parts by weight, the composition paste has lower fluidity, which makes sufficient mixing difficult, and therefore the acid-base reaction may not proceed smoothly. As a result, the cured product may have reduced strength.

With respect to 100 parts by weight of the whole amount of polymerizable monomer components, the content of solvent (E) is preferably 7 to 500 parts by weight, more preferably 10 to 300 parts by weight, and further preferably 20 to 100 parts by weight. When the solvent (E) is contained in such ranges, the acid-base reaction can proceed smoothly, and the resultant cured product has excellent mechanical strength and excellent adhesive properties to a tooth structure.

With respect to 100 parts by weight of the whole amount of polymerizable monomer components, the content of the aforementioned polyalkenoic acid is preferably 1 to 200 parts by weight, more preferably 5 to 100 parts by weight, and further preferably 10 to 50 parts by weight. When the polyalkenoic acid is contained in such ranges, curing through the acid-base reaction proceeds smoothly and decay of the resultant cured product inside an oral cavity by, for example, hydrolysis can be diminished.

As described above, since curing of a glass ionomer cement occurs through progress of an acid-base reaction, from the viewpoint of storage stability, it is preferable that a filler (H) and polyalkenoic acid be packed in separate containers and be used after being mixed immediately before use. The preferable types of products to be employed include a so-called powder-liquid type, but from the viewpoint of improving handling ability, the form of so-called two past-type glass ionomer cement containing two types of pastes is more preferable. In the case where the type of product is the two paste type, when the aforementioned two pastes are referred to as a paste A and a paste B, respectively, an embodiment is preferable in which the paste A contains (A), (B), (C), (G), (H), (E) and polyalkenoic acid and the paste B contains (A), (B), (F) and (H). Furthermore, an embodiment in which the paste A contains (A), (B), (C), (F), (H), (E) and polyalkenoic acid and the paste B contains (A), (B), (G) and (H) also is used preferably. In either of the embodiments, since the paste A contains polyalkenoic acid, it is preferable that at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass be used as the filler (H) contained in the paste B, and it is more preferable that fluoroaluminosilicate glass and/or barium fluoroaluminosilicate glass be used as the filler (H). On the other hand, the filler (H) contained in the paste A to be used is preferably one that exhibits no reactivity with polyalkenoic acid, and particularly preferably quartz.

These dental materials can be prepared and used according to a conventional method. These dental materials exhibit excellent bond strength and bond durability with respect to a tooth structure (particularly dentin). Hereinafter, the present invention is described in further detail using examples but is not limited thereto.

EXAMPLE 1

Application to One-Step Bonding System
(One-Component Bonding Material)

(1) Production of One-Component Bonding Material

Respective components were mixed together at an ordinary temperature and thereby a one-component bonding material composition was produced. The composition thereof is indicated in Table 1. The bond strength with respect to bovine teeth dentin was measured according to the following procedure.

TABLE 1

One-Component Bonding Material Compositions and Bonding Evaluation Results

| Components | | Example 1-1 | Example 1-2 | Example 1-3 | Example 1-4 | Example 1-5 | Example 1-6 |
|---|---|---|---|---|---|---|---|
| Plymerizable monomer (A) | EDMA | 15 | | | | 15 | 15 |
| | XDMA | | 15 | | | | |
| | SDMA | | | 15 | | | |
| | MDMA | | | | 15 | | |
| Polymerizable monomer for comparison with (A) | #801 | | | | | | |
| | GDMA | | | | | | |
| | ErMA | | | | | | |
| | Trimethylolpropane trimethacrylate | | | | | | |
| Polymerizable monomer (B) having one polymerizable group and at least one hydroxyl group | HEMA | 15 | 15 | 15 | 15 | 15 | 15 |
| Polymerizable monomer (C) having acidic group | MDP | 10 | 10 | 10 | 10 | 10 | 10 |
| Crosslinkable polymerizable monomer (D) | Bis-GMA | 30 | 30 | 30 | 30 | 30 | 30 |
| Solvent (E) | Distilled water | 15 | 15 | 15 | 15 | 15 | 15 |
| | Ethanol | 15 | 15 | 15 | 15 | 15 | 15 |
| Polymerization initiator (F) | TMDPO | 5 | 5 | 5 | 5 | | 3 |
| | CQ | | | | | 2 | 2 |
| Polymerization accelerator (G) | DBB | | | | | 1 | 1 |
| Filler (H) | Inorganic filler 1 | 5 | 5 | 5 | 5 | 5 | 5 |
| Bond strength with respect to dentin (MPa) | After 24 hours | 18.7 | 16.5 | 17.5 | 19.9 | 18.5 | 18.9 |
| | After thermal cycles load | 19.0 | 18.2 | 18.4 | 19.5 | 18.6 | 18.8 |

| Components | | C. Example 1-1 | C. Example 1-2 | C. Example 1-3 | C. Example 1-4 | C. Example 1-5 | C. Example 1-6 |
|---|---|---|---|---|---|---|---|
| Plymerizable monomer (A) | EDMA | 30 | | | | | |
| | XDMA | | | | | | |
| | SDMA | | | | | | |
| | MDMA | | | | | | |
| Polymerizable monomer for comparison with (A) | #801 | | 15 | | | | |
| | GDMA | | | 15 | | | |
| | ErMA | | | | 15 | | |
| | Trimethylolpropane trimethacrylate | | | | | 15 | |
| Polymerizable monomer (B) having one polymerizable group and at least one hydroxyl group | HEMA | | 15 | 15 | 15 | 15 | 30 |

TABLE 1-continued

| One-Component Bonding Material Compositions and Bonding Evaluation Results | | | | | | | |
|---|---|---|---|---|---|---|---|
| Polymerizable monomer (C) having acidic group | MDP | 10 | 10 | 10 | 10 | 10 | 10 |
| Crosslinkable polymerizable monomer (D) | Bis-GMA | 30 | 30 | 30 | 30 | 30 | 30 |
| Solvent (E) | Distilled water | 15 | 15 | 15 | 15 | 15 | 15 |
| | Ethanol | 15 | 15 | 15 | 15 | 15 | 15 |
| Polymerization initiator (F) | TMDPO | 5 | 5 | 3 | 5 | 5 | 5 |
| | CQ | | | 2 | | | |
| Polymerization accelerator (G) | DBB | | | 1 | | | |
| Filler (H) | Inorganic filler 1 | 5 | 5 | 5 | 5 | 5 | 5 |
| Bond strength with respect to dentin (MPa) | After 24 hours | 12.9 | 10.2 | 12.7 | 12.8 | 12.1 | 12.9 |
| | After thermal cycles load | 15.1 | 9.5 | 9.7 | 11.2 | 11.0 | 8.6 |

(The amounts of respective components added each are indicated in the unit of parts by weight.)
EDMA: erythritol dimethacrylate [1,4-bis(methacryloyloxy)-2,3-butanediol]
XDMA: xylitol dimethacrylate [1,5-bis(methacryloyloxy)-2,3,4-pentanetriol]
SDMA: sorbitol dimethacrylate [1,6-bis(methacryloyloxy)-2,3,4,5-hexanetetraol]
MDMA: mannitol dimethacrylate (3,4-di-O-methacryloyl-D-mannitol)
801: 1,2-bis(3-methacryloyloxy-2-hydroxypropoxy)ethane
GDMA: glycerol dimethacrylate [polymerizable monomer for comparative examples that does not correspond to polymerizable monomer (A)]
ErMA: pentaerythritol dimethacrylate
HEMA: 2-hydroxyethylmethacrylate
MDP: 10-methacryloyloxydecyldihydrogenphosphate
Bis-GMA: 2,2-bis[4-(3-methacryloyloxy)-2-hydroxypropoxyphenyl]propane (bisphenol A diglycidyl methacrylate)
TMDPO: 2,4,6-trimethylbenzoyldiphenylphosphine oxide
CQ: camphorquinone
DBB: N,N-dimethylaminobenzoic acid n-butoxyethyl ester
Inorganic filler 1: "R972" manufactured by Japan Aerosil Inc.
MDMA is a new compound and it was synthesized by the following method.

REFERENCE EXAMPLE

Synthesis of MDMA (i) Synthesis of 1,2:5,6-Di-O-isopropylidene-3,4-di-O-methacryloyl-D-mannitol After 700 mL of anhydrous pyridine was added to a 2 L separable flask equipped with a condenser tube, 65 g of 1,2:5,6-Di-O-isopropylidene-D-mannitol (manufactured by Wako Pure Chemical Industries, Ltd.) was added into the flask gradually and was dissolved completely. An ice bath was set for the reaction system and the reaction system was cooled to 0° C. Subsequently, while the temperature of the reaction system was maintained around 0° C. and the reaction system was stirred, 60 g of methacryloyl chloride (manufactured by Wako Pure Chemical Industries, Ltd.) was dropped into the reaction system in a nitrogen atmosphere using a dropping funnel over approximately one hour. The dropping funnel was replaced by a glass stopper, and the reaction system was heated to 70° C. using an oil bath. This heating was continued for eight hours. After completion of heating, the oil bath was removed and the reaction system was then cooled to room temperature. Subsequently, the reaction system was poured into a beaker containing 1 L of ice water and thereby the reaction was stopped. After the reaction was stopped, extraction was performed five times using 1500 mL of diethyl ether. Thereafter, the resultant organic layer was subjected to vacuum concentration using an evaporator and thus an oily material was obtained. The oily material was purified using silica gel column chromatography (diluents: hexane:diethyl ether=7:3). After concentration, hexane was added and thereby recrystallization was carried out. Thus, a target compound was obtained. The yield amount was 36.3 g, and the yield rate was 37%.

$^1$H-NMR (400 MHz, CDCl$_3$, δ) 1.31 (s, 6H), 1.36 (s, 6H), 1.96 (s, 6H), 3.85-3.96 (m, 4H), 4.21-4.27 (m, 2H), 5.43 (dd, 2H), 5.64 (s, 2H), 6.15 (s, 2H) (ppm)
$^{13}$C-NMR (100 MHz, CDCl$_3$, δ) 18.2, 25.1, 26.3, 65.5, 71.6, 74.7, 109.3, 126.6, 135.6, 166.0 (ppm)

(ii) Synthesis of MDMA (3,4-di-O-methacryloyl-D-mannitol)

540 mL of acetic acid and 180 mL of water were added to a 2 L round-bottom flask. While the resultant acetic acid aqueous solution was stirred, 18 g of 1,2:5,6-Di-O-isopropylidene-3,4-di-O-methacryloyl-D-mannitol synthesized above was added gradually thereto and was dissolved completely. The solution thus prepared was stirred for 18 hours, with the temperature thereof being maintained at 25° C. After completion of stirring, the solution was subjected to vacuum concentration using an evaporator and thus an oily material was obtained. The oily material was purified using silica gel column chromatography (diluent: ethyl acetate 100%) and was concentrated. As a result, white crystals were precipitated. It was confirmed by NMR that these crystals were a target compound. The yield amount was 8.7 g and the yield rate was 60%.

$^1$H-NMR (400 MHz, CD$_3$OD, δ) 1.84 (s, 6H), 3.39 (dd, 2H), 3.51 (dd, 2H), 3.59-3.66 (m, 2H), 5.28 (d, 2H), 5.56 (s, 2H), 6.03 (s, 2H) (ppm)
$^{13}$C-NMR (100 MHz, CD$_3$OD, δ) 18.4, 64.2, 71.6, 73.1, 126.8, 137.4, 167.9 (ppm)

(2) Method of Evaluating Bonding to Bovine Teeth Dentin

The labial surface of a bovine mandibular incisor was ground with #80 silicon carbide paper (manufactured by Nihon Kenshi Co., Ltd.) under running water, and thereby a sample with an exposed flat surface of dentin was obtained. The sample thus obtained further was ground with #1000 silicon carbide paper (manufactured by Nihon Kenshi Co., Ltd.) under running water. After completion of grinding, water on the surface was air-blown to be dried. An adhesive tape with a thickness of about 150 μm having a circular hole whose diameter was 3 mm was attached to the smooth surface that had been dried and thereby the adhesive area was defined.

Each one-component bonding material composition produced above was applied into the above-mentioned circular hole using a brush and was then allowed to stand for 20 seconds. Thereafter, the surface thereof was air-blown with a dental air syringe and thereby the one-component bonding material composition thus applied was dried until it lost fluidity. Subsequently, it was irradiated with light using a dental visible light unit "JET LITE 3000" (manufactured by J. Morita USA) for 10 seconds. Thus, the one-component bonding material composition that had been applied was cured.

A dental filling composite resin (manufactured by Kuraray Medical Inc., "CLEARFIL AP-X" (trade name, registered trademark)) was applied to the surface of each resultant cured product of the one-component bonding material compositions, and it was then covered with a mold release film (polyester). Next, slide glass was placed on the mold release film to press it, and thereby the surface of the applied composite resin was smoothed. Subsequently, the composite resin was irradiated with light for 20 seconds using the aforementioned unit "JET LITE 3000" through the mold release film. Thus, the composite resin was cured.

One end face (circular section) of a stainless-steel cylindrical rod (with a diameter of 5 mm and a length of 1.5 cm) was bonded to the surface of the resultant cured product of the dental filling composite resin using a commercially available dental resin cement (manufactured by Kuraray Medical Inc., "PANAVIA21" (trade name)). After bonding, this sample was allowed to stand still at room temperature for 30 minutes and was then immersed in distilled water. The resultant sample that had been immersed in distilled water was allowed to stand still for 24 hours inside a thermostat whose temperature was maintained at 37° C. Thus, a bonding test sample was produced. Ten bonding test samples were produced in total, and all the samples that had been immersed in distilled water were allowed to stand still for 24 hours inside the thermostat whose temperature was maintained at 37° C. With respect to five samples out of the ten samples, in order to evaluate the bond strength in the early bonding stage, the bond strength was measured immediately after they were allowed to stand still for 24 hours. With respect to the other five samples, in order to evaluate bond durability, bond strength was measured after 4000 thermal cycles had been performed, with one cycle being a process for further immersing each sample in 4° C. cold water and 60° C. warm water alternately for one minute.

(3) Measurement of Bond Strength

The tensile bond strengths of the above-mentioned five bonding test samples were measured with a universal testing machine (manufactured by Instron Inc.), with the crosshead speed being set at 2 mm/min, and the average value thereof was taken as tensile bond strength. The results thus obtained are indicated together in Table 1.

EXAMPLE 2

Application to Two-Step Bonding System (Two-Component Bonding Material)

(1) Production of Primer Using Polymerizable Composition Containing Polymerizable Monomer (A)

The respective components were mixed together at ordinary temperature and thereby primer compositions were produced. The compositions thereof are indicated in Table 2.

TABLE 2

Primer Compositions and Bonding Evaluation Results

| | Components | Example 2-1 | Example 2-2 | Example 2-3 | Example 2-4 | Example 2-5 | C. Example 2-1 | C. Example 2-2 | C. Example 2-3 |
|---|---|---|---|---|---|---|---|---|---|
| Plymerizable monomer (A) | EDMA | 35 | | | | 35 | | | |
| | XDMA | | 35 | | | | | | |
| | SDMA | | | 35 | | | | | |
| | MDMA | | | | 35 | | | | |
| Polymerizable monomer for comparison with (A) | GDMA | | | | | | 35 | | |
| | ErMA | | | | | | | 35 | |
| Polymerizable monomer (B) having one polymerizable group and at least one hydroxyl group | HEMA | 35 | 35 | 35 | 35 | 35 | 35 | 35 | 70 |
| Polymerizable monomer (C) having acidic group | MDP | 20 | 20 | 20 | 20 | 20 | 20 | 20 | 20 |
| Crosslinkable polymerizable monomer (D) | #801 | 10 | 10 | 10 | 10 | 10 | 10 | 10 | 10 |
| Solvent (E) | Distilled water | 50 | 50 | 50 | 50 | 50 | 50 | 50 | 50 |
| | Ethanol | 50 | 50 | 50 | 50 | 50 | 50 | 50 | 50 |
| Polymerization initiator (F) | TMDPO | 0.8 | 0.8 | 0.8 | 0.8 | | 0.8 | 0.8 | 0.8 |
| | CQ | | | | | 0.8 | | | |
| Polymerization accelerator (G) | DBB | | | | | 1 | | | |
| Bond strength with respect to dentin (MPa) | After 24 hours | 23.6 | 21.2 | 20.3 | 22.7 | 23.9 | 13.8 | 14.9 | 14.4 |
| | After thermal cycles load | 23.9 | 21.8 | 20.4 | 21.5 | 22.4 | 9.3 | 12.4 | 8.7 |

(The amounts of respective components added each are indicated in the unit of parts by weight, and the respective abbreviations have the same meanings as described above.)

(2) Method of Evaluating Bonding to Bovine Teeth Dentin

The labial surface of a bovine mandibular incisor was ground with #80 silicon carbide paper (manufactured by Nihon Kenshi Co., Ltd.) under running water, and thereby a sample with an exposed flat surface of dentin was obtained. The sample thus obtained further was ground with #1000 silicon carbide paper (manufactured by Nihon Kenshi Co., Ltd.) under running water. After completion of grinding, water on the surface was air-blown to be dried. An adhesive tape with a thickness of about 150 μm having a circular hole whose diameter was 3 mm was attached to the smooth surface that had been dried and thereby the adhesive area was defined.

Each primer produced above was applied into the above-mentioned circular hole using a brush and was then allowed to stand for 20 seconds. Thereafter, the surface thereof was air-blown and thereby the primer thus applied was dried until it lost fluidity. Next, the bonding material having a composition indicated in Table 3 was applied over the tooth surface where the primer had been applied and dried. Subsequently, it was irradiated with light using a dental visible light unit "JET LITE 3000" (manufactured by J. Morita USA) for 10 seconds. Thus, the primer and bonding material that had been applied were cured.

A dental filling composite resin (manufactured by Kuraray Medical Inc., "CLEARFIL AP-X" (trade name, registered trademark)) was applied to the surface of the resultant cured product of the bonding material, and it was then covered with a mold release film (polyester). Next, slide glass was placed on the mold release film to press it, and thereby the surface of the applied composite resin was smoothed. Subsequently, the composite resin was irradiated with light for 20 seconds using the aforementioned unit "JET LITE 3000" through the mold release film. Thus, the composite resin was cured.

One end face (circular section) of a stainless-steel cylindrical rod (with a diameter of 7 mm and a length of 2.5 cm) was bonded to the surface of the resultant cured product of the dental filling composite resin using a commercially available dental resin cement (manufactured by Kuraray Medical Inc., "PANAVIA21" (trade name)). After bonding, this sample was allowed to stand still at room temperature for 30 minutes and was then immersed in distilled water. Ten bonding test samples were produced in total, and all the samples that had been immersed in distilled water were allowed to stand still for 24 hours inside a thermostat whose temperature was maintained at 37° C. With respect to five samples out of the ten samples, in order to evaluate the bond strength in the early bonding stage, the bond strength was measured immediately after they were allowed to stand still for 24 hours. With respect to the other five samples, in order to evaluate bond durability, bond strength was measured after 4000 thermal cycles had been performed, with one cycle being a process for further immersing each sample in 4° C. cold water and 60° C. warm water alternately for one minute.

TABLE 3

| Composition of Bonding Material | |
| --- | --- |
| Components | Amount added (parts by weight) |
| HEMA | 40 |
| Bis-GMA | 40 |
| NPG | 20 |
| Photoinitiator (TMDPO) | 3 |
| Inorganic filler 1 | 5.5 |
| Inorganic filler 2 | 1.5 |

NPG: neopentyl glycol dimethacrylate

Inorganic filler 2: "Ar380" manufactured by Japan Aerosil Inc.

(The other abbreviations have the same meanings as described above.)

(3) Bonding Evaluation Test (Evaluations of Bond Strength and Bond durability)

The tensile bond strengths of the above-mentioned bonding test samples were measured with a universal testing machine (manufactured by Shimadzu Corporation), with the crosshead speed being set at 2 mm/min, and the average value thereof was taken as tensile bond strength.

EXAMPLE 3

Application of Polymerizable Composition Containing Polymerizable Monomer (A) to Dental Self-Adhesive Composite Resin (1) Preparation of Dental Self-Adhesive Composite Resin The inorganic particles and polymerizable monomer compositions indicated in Table 4 were mixed together, respectively, and thereby paste-like dental composite resins were prepared. The bond strength with respect to dentin is indicated together.

TABLE 4

| Composite Resin Compositions and Bonding Evaluation Results | | | | | | | | | | |
| --- | --- | --- | --- | --- | --- | --- | --- | --- | --- | --- |
| | | Example 3-1 | Example 3-2 | Example 3-3 | Example 3-4 | Example 3-5 | C. Example 3-1 | C. Example 3-2 | C. Example 3-3 | C. Example 3-4 |
| Polymerizable monomer (A) | EDMA | 25 | | | | | 25 | | | 25 |
| | MDMA | | 25 | | | | | | | |
| | XDMA | | | 25 | | | | | | |
| | SDMA | | | | 25 | | | | | |
| Polymerizable monomer for comparison with (A) | GDMA | | | | | | | 25 | | |
| | #801 | | | | | | | | 25 | |
| Polymerizable monomer (B) having one polymerizable group and at least one hydroxyl group | HEMA | 25 | 25 | 25 | 25 | 25 | 50 | 25 | 25 | |

TABLE 4-continued

Composite Resin Compositions and Bonding Evaluation Results

|  |  | Example 3-1 | Example 3-2 | Example 3-3 | Example 3-4 | Example 3-5 | C. Example 3-1 | C. Example 3-2 | C. Example 3-3 | C. Example 3-4 |
|---|---|---|---|---|---|---|---|---|---|---|
| Polymerizable monomer (C) having acidic group | MDP | 10 | 10 | 10 | 10 | 10 | 10 | 10 | 10 | 10 |
| Crosslinkable polymerizable monomer (D) | 3G |  |  |  |  |  |  |  |  | 25 |
|  | Bis-GMA | 40 | 40 | 40 | 40 | 40 | 40 | 40 | 40 | 40 |
| Polymerization initiator (F) | TMDPO |  |  |  |  | 1 |  |  | 1 |  |
|  | CQ | 1 | 1 | 1 | 1 | 0.5 | 1 | 1 | 0.5 | 1 |
| Polymerization accelerator (G) | PDE | 1 | 1 | 1 | 1 | 0.5 | 1 | 1 | 0.5 | 1 |
| Filler (H) | Inorganic filler 3 | 230 | 230 | 230 | 230 | 230 | 230 | 230 | 230 | 230 |
|  | Inorganic filler 4 | 20 | 20 | 20 | 20 | 20 | 20 | 20 | 20 | 20 |
| Polymerization inhibitor | BHT |  |  |  |  | 0.03 |  |  | 0.03 |  |
| Bond strength with respect to dentin (MPa) (No Adhesive) |  | 12.3 | 11.5 | 10.8 | 10.9 | 11.9 | 9.3 | 8.5 | 8.1 | 6.9 |
| Bending Strength (MPa) |  | 100 | 98 | 96 | 95 | 95 | 92 | 103 | 99 | 98 |

PDE: ethyl p-(N,N-dimethylamino)benzoate
Inorganic filler 3: Silane-treated barium glass powder
Barium glass (manufactured by STEC, Product Code: "Raysorb E-3000") was crushed with a ball mill and thus barium glass powder was obtained. The mean particle size of the barium glass powder thus obtained was measured with a laser diffraction particle size distribution analyzer (manufactured by Shimadzu Corporation, Type "SALD-2100") and it was 2.4 μm. The surface treatment was performed by a conventional method using 3 parts by weight of 3-methacryloyloxypropyltrimethoxysilane with respect to 100 parts by weight of this barium glass powder. Thus, silane-treated barium glass powder was obtained.
Inorganic filler 4: Silane-treated colloidal silica powder
0.3 part by weight of acetic acid and 3 parts by weight of 3-methacryloyloxypropyltrimethoxysilane were added to 100 parts by weight of distilled water, which was then stirred. Further 50 parts by weight of colloidal silica powder (manufactured by Japan Aerosil Inc., Product Code: "Aerosil OX50") was added thereto, which was then stirred for one hour. After water was removed by lyophilization, this was heat-treated at 80° C. for five hours and thus silane-treated colloidal silica powder was obtained.
(The amounts of respective components added each are indicated in the unit of parts by weight, and the other abbreviations have the same meanings as described above.)

(2) Method of Evaluating Bonding to Bovine Teeth Dentin

A bovine incisor was wet-ground with #1000 silicon carbide paper (manufactured by Nihon Kenshi Co., Ltd.) to be smooth and thereby an enamel surface or dentin surface was exposed. Thereafter, water on the surface was blown away using a dental air syringe. An adhesive tape with a thickness of about 150 μm having a circular hole whose diameter was 3 mm was attached to the exposed enamel surface or dentin surface. Each self-adhesive composite resin composition produced above was placed in the circular hole and this was covered with a mold release film (manufactured by Kuraray Co., Ltd., "EVAL" (trade name)). Thereafter, slide glass was placed on the mold release film to press it, and this was irradiated with light for 20 seconds using the dental light unit (manufactured by MORITA Corp., "JET LITE 3000" (trade name)). Thus, the composite resin was cured. Next, one end face (circular section) of a stainless-steel cylindrical rod with a diameter of 5 mm and a length of 1.5 cm was bonded to the cured surface using a dental resin cement (manufactured by Kuraray Medical Inc., "PANAVIA21" (trade name)). This was allowed to stand still for 30 minutes and thus a test piece was obtained. Five bonding test samples were produced in total.

(3) Bonding Evaluation Test

The tensile bond strengths of the above-mentioned bonding test samples were measured with a universal testing machine (manufactured by Shimadzu Corporation), with the crosshead speed being set at 2 mm/min, and the average value thereof was taken as tensile bond strength.

EXAMPLE 4

Application of Polymerizable Composition Containing Polymerizable Monomer (A) to Dental Self-Adhesive Cement (1) Preparation of Dental Self-Adhesive Cement The respective components indicated in Table 5 were mixed together at ordinary temperature and thereby a paste A and a paste B were prepared. Next, these pastes were mixed and thereby a cement composition that is a dental composition was prepared, and the bond strength with respect to bovine teeth dentin was measured.

TABLE 5

Dental Self-Adhesive Cement Compositions and Bonding Evaluation Results

|  | Components |  | Example 4-1 | Example 4-2 | Example 4-3 | Example 4-4 | Example 4-5 | Example 4-6 | C. Example 4-1 | C. Example 4-2 |
|---|---|---|---|---|---|---|---|---|---|---|
| A | Polymerizable monomer (A) | EDMA | 20 |  |  |  | 20 | 20 |  |  |
|  |  | MDMA |  | 20 |  |  |  |  |  |  |
|  |  | XDMA |  |  | 20 |  |  |  |  |  |
|  |  | SDMA |  |  |  | 20 |  |  |  |  |
|  | Polymerizable monomer for comparison with (A) | GDMA |  |  |  |  |  |  | 20 |  |
|  | Polymerizable monomer (B) having one | HEMA | 50 | 50 | 50 | 50 | 50 | 50 | 50 | 70 |

TABLE 5-continued

Dental Self-Adhesive Cement Compositions and Bonding Evaluation Results

| | Components | | Example 4-1 | Example 4-2 | Example 4-3 | Example 4-4 | Example 4-5 | Example 4-6 | C. Example 4-1 | C. Example 4-2 |
|---|---|---|---|---|---|---|---|---|---|---|
| | polymerizable group and at least one hydroxyl group | | | | | | | | | |
| | Polymerizable monomer (C) having acidic group | MDP | 30 | 30 | 30 | 30 | 30 | 30 | 30 | 30 |
| | Polymerization initiator (F) | THP | 5 | 5 | 5 | 5 | | | 5 | 5 |
| | | CHP | | | | | 5 | | | |
| | | BPO | | | | | | 2 | | |
| | Filler (H) | Inorganic filler 3 | 140 | 140 | 140 | 140 | 140 | 140 | 140 | 140 |
| | | Inorganic filler 4 | 45 | 45 | 45 | 45 | 45 | 45 | 45 | 45 |
| | Stabilizer | BHT | 0.2 | 0.2 | 0.2 | 0.2 | 0.2 | 0.2 | 0.2 | 0.2 |
| B | Polymerizable monomer (B) having one polymerizable group and at least one hydroxyl group | HEMA | 50 | 50 | 50 | 50 | 50 | 50 | 50 | 50 |
| | Crosslinkable polymerizable monomer (D) | D-2.6E | 50 | 50 | 50 | 50 | 50 | 50 | 50 | 50 |
| | Polymerization accelerator (G) | PTU | 1 | 1 | 1 | 1 | 1 | | 1 | 1 |
| | | DEPT | | | | | | 0.4 | | |
| | | TPBSS | | | | | | 1 | | |
| | Filler (H) | Inorganic filler 3 | 140 | 140 | 140 | 140 | 140 | 140 | 140 | 140 |
| | | Inorganic filler 4 | 45 | 45 | 45 | 45 | 45 | 45 | 45 | 45 |
| | Stabilizer | BHT | 0.05 | 0.05 | 0.05 | 0.05 | 0.05 | 0.05 | 0.05 | 0.05 |
| Bond strength with respect to dentin (MPa) | | After 24 hours | 5.4 | 7.5 | 4.9 | 4.6 | 5.0 | 6.5 | 1.4 | 4.0 |
| | | After thermal cycles load | 5.3 | 7.1 | 4.5 | 4.4 | 4.5 | 6.0 | 1.2 | 1.5 |

THP: 1,1,3,3-tetramethylbutyl hydroperoxide
CHP: cumene hydroperoxide
BPO: benzoyl peroxide
BHT: dibutylhydroxytoluene (4-methyl-2,6-di-tert-butylphenol)
D-2.6E: 2,2-bis(4-methacryloyloxypolyethoxyphenyl)propane {average number of oxyethylene chain units of 2.6}
PTU: 1-(2-pyridyl)-2-thiourea
DEPT: N,N-diethanol-p-toluidine
TPBSS: sodium 2,4,6-triisopropyl benzenesulfinate
(The amounts of respective components added each are indicated in the unit of parts by weight, and the other abbreviations have the same meanings as described above.)

(2) Method of Evaluating Bonding to Bovine Teeth Dentin

The labial surface of a bovine mandibular incisor was ground with #80 silicon carbide paper (manufactured by Nihon Kenshi Co., Ltd.) under running water, and thereby a sample with an exposed flat surface of dentin was obtained. The sample thus obtained further was ground with #1000 silicon carbide paper (manufactured by Nihon Kenshi Co., Ltd.) under running water. After completion of grinding, water on the surface was air-blown to be dried. An adhesive tape with a thickness of about 150 μm having a circular hole whose diameter was 3 mm was attached to the smooth surface that had been dried and thereby the adhesive area was defined.

A cement composition obtained by mixing the paste A and the paste B that had been produced as described above at a mass ratio of 1:1 was applied in a mound form onto one end face (circular section) of a stainless-steel cylindrical rod (with a diameter of 7 mm and a length of 2.5 cm). The end face on which the mound of cement composition was made was placed on the circular hole to press it so that the center of the stainless-steel cylindrical rod coincided with the center of the circular hole. Thus, the stainless-steel cylindrical rod was set vertically to the tooth surface.

After setting the stainless-steel cylindrical rod, excess cement composition flowing out around the rod was removed with an instrument, and this sample was allowed to stand still at room temperature for 30 minutes and was then immersed in distilled water. Ten bonding test samples were produced in total, and all the samples that had been immersed in distilled water were allowed to stand still for 24 hours inside a thermostat whose temperature was maintained at 37° C. With respect to five samples out of the ten samples, in order to evaluate the bond strength in the early bonding stage, the bond strength was measured immediately after they were allowed to stand still for 24 hours. With respect to the other five samples, in order to evaluate bond durability, bond strength was measured after 4000 thermal cycles had been performed, with one cycle being a process for further immersing each sample in 4° C. cold water and 60° C. warm water alternately for one minute.

(3) Bonding Evaluation Test (Evaluations of Bond Strength and Bond Durability)

The tensile bond strengths of the above-mentioned five bonding test samples were measured with a universal testing machine (manufactured by Shimadzu Corporation), with the crosshead speed being set at 2 mm/min, and the average value thereof was taken as tensile bond strength.

EXAMPLE 5

Application to Dental Resin-Reinforced Glass Ionomer Cement (1) Preparation of Powder-Liquid Type Resin-Reinforced Glass Ionomer Cement

EXAMPLES 5-1 AND COMPARATIVE EXAMPLES 5-1 AND 5-2

The respective components indicated in Table 6 were mixed together at ordinary temperature and thereby a liquid material was prepared. 2.5 parts by weight of DEPT (N,N-di (2-hydroxyethyl)-p-toluidine) and 1.5 parts by weight of BSS (sodium benzenesulfinate) were added to a mixed solvent containing 80 parts by weight of toluene and 20 parts by weight of methanol, and the resultant mixture was stirred for 10 minutes. Next, 500 parts by weight of fluoroaluminosilicate powder (manufactured by SCHOTT, Product Code "G018-117") (hereinafter also referred to as FAS glass) was added thereto, and the resultant mixture was stirred for 10 minutes. After the solvent was distilled off under reduced pressure, the resultant mixture was dried. Thereafter, it was subjected to sieving with a mesh (#150) and thereby a powder material was prepared. Next, a dental resin-reinforced glass ionomer cement was prepared by mixing these liquid material and powder material at a mass ratio of 1:3. The bond strength with respect to bovine teeth dentin was measured according to the following procedure.

TABLE 6

Powder-Liquid Type Resin-Reinforced Glass Ionomer Cement Compositions and Bonding Evaluation Results

|  |  | Example 5-1 | C. Example 5-1 | C. Example 5-2 |
|---|---|---|---|---|
| Polymerizable monomer (A) | EDMA | 30 |  |  |
| Polymerizable monomer for comparison with (A) | GDMA |  |  | 30 |
| Polymerizable monomer (B) having one polymerizable group and at least one hydroxyl group | HEMA | 35 | 65 | 35 |
| Solvent (E) | Water | 20 | 20 | 20 |
| Polymerization initiator (F) | BPO | 3 | 3 | 3 |
| Polyalkenoic acid | Polyacrylic acid | 35 | 35 | 35 |
| Stabilizer | BHT | 0.05 | 0.05 | 0.05 |
| Bond strength with respect to dentin (MPa) | After 24 hours | 4.6 | 3.9 | 1.4 |
|  | After thermal cycles load | 4.0 | 0.5 | 0.9 |

(The amounts of respective components added each are indicated in the unit of parts by weight, and the respective abbreviations have the same meanings as described above.)

(2) Preparation of Two Paste Type Resin-Reinforced Glass Ionomer Cement

EXAMPLES 5-2 to 5-6 AND COMPARATIVE EXAMPLE 5-3

The respective components indicated in Table 7 were mixed together at ordinary temperature and thereby a paste A and a paste B were produced. Next, a dental resin-reinforced glass ionomer cement was prepared by mixing these pastes at a mass ratio of 1:1. The bond strength with respect to bovine teeth dentin was measured according to the following procedure.

TABLE 7

Two Paste Type Resin-Reinforced Glass Ionomer Cement Compositions and Bonding Evaluation Results

|  | Components |  | Example 5-2 | Example 5-3 | Example 5-4 | Example 5-5 | Example 5-6 | Example 5-7 | Example 5-8 | C. Example 5-3 |
|---|---|---|---|---|---|---|---|---|---|---|
| A | Polymerizable monomer (B) having one polymerizable group and at least one hydroxyl group | HEMA | 35 | 50 | 50 | 50 | 50 | 50 | 50 | 50 |
|  | Polymerizable monomer (C) having acidic group | MDP | 25 | — | — | — | — | — | — | — |
|  | Polymerization initiator (F) | BPO | 2 | 2 | 2 | 2 | 2 | 2 | — | 2 |
|  |  | THP | — | — | — | — | — | — | 5 | — |
|  | Filler (H) | Inorganic filler 3 | 220 | 220 | 220 | 220 | 220 | 220 | 220 | 220 |
|  |  | Inorganic filler 1 | 15 | 15 | 15 | 15 | 15 | 15 | 15 | 15 |
|  | Stabilizer | BHT | 0.05 | 0.05 | 0.05 | 0.05 | 0.05 | 0.05 | 0.05 | 0.05 |
|  | Polyalkenoic acid | Polyacrylic acid | 40 | 50 | 50 | 50 | 50 | 50 | 50 | 50 |
| B | Polymerizable monomer (A) | EDMA | 40 | 40 | — | — | — | 40 | 40 | — |
|  |  | XDMA | — | — | 40 | — | — | — | — | — |
|  |  | SDMA | — | — | — | 40 | — | — | — | — |
|  |  | MDMA | — | — | — | — | 40 | — | — | — |

TABLE 7-continued

Two Paste Type Resin-Reinforced Glass Ionomer Cement Compositions and Bonding Evaluation Results

| Components | | Example 5-2 | Example 5-3 | Example 5-4 | Example 5-5 | Example 5-6 | Example 5-7 | Example 5-8 | C. Example 5-3 |
|---|---|---|---|---|---|---|---|---|---|
| Polymerizable monomer for comparison with (A) | GDMA | — | — | — | — | — | — | — | 40 |
| Polymerizable monomer (B) having one polymerizable group and at least one hydroxyl group | HEMA | 40 | 40 | 40 | 40 | 40 | 40 | 40 | 40 |
| Crosslinkable polymerizable monomer (D) | Bis-GMA | 20 | 20 | 20 | 20 | 20 | 20 | 20 | 20 |
| Solvent (E) | Water | 20 | — | — | — | — | 20 | — | — |
| Polymerization accelerator | DEPT | 0.5 | 0.5 | 0.5 | 0.5 | 0.5 | 0.5 | — | 0.5 |
| (G) | TPBSS | 0.5 | 0.5 | 0.5 | 0.5 | 0.5 | 0.5 | — | 0.5 |
| | PTU | — | — | — | — | — | — | 1 | — |
| Filler (H) | FAS glass | 220 | 220 | 220 | 220 | 220 | 220 | 220 | 220 |
| | Inorganic filler 1 | 15 | 15 | 15 | 15 | 15 | 15 | 15 | 15 |
| Stabilizer | BHT | 0.05 | 0.05 | 0.05 | 0.05 | 0.05 | 0.05 | 0.05 | 0.05 |
| Bond strength with respect to dentin (MPa) | | 5.5 | 4.4 | 4.1 | 3.9 | 4.2 | 4.6 | 4.5 | 1.7 |

(The amounts of respective components added each are indicated in the unit of parts by weight, and the respective abbreviations have the same meanings as described above.)

(3) Production of Sample for Evaluating Bonding to Bovine Teeth Dentin

The labial surface of a bovine mandibular incisor was ground with #80 silicon carbide paper (manufactured by Nihon Kenshi Co., Ltd.) under running water, and thereby a sample with an exposed flat surface of dentin was obtained. The sample thus obtained further was ground with #1000 silicon carbide paper (manufactured by Nihon Kenshi Co., Ltd.) under running water. After completion of grinding, water on the surface was air-blown to be dried. An adhesive tape with a thickness of about 150 μm having a circular hole whose diameter was 3 mm was attached to the smooth surface that had been dried and thereby the adhesive area was defined.

The dental resin-reinforced glass ionomer cements of Examples and Comparative Example that had been prepared as described above each were applied in a mound form onto one end face (circular section) of a stainless-steel cylindrical rod (with a diameter of 7 mm and a length of 2.5 cm). The end face on which the mound of cement composition was made was placed on the circular hole to press it so that the center of the stainless-steel cylindrical rod coincided with the center of the circular hole. Thus, the stainless-steel cylindrical rod was set vertically to the tooth surface.

After setting the stainless-steel cylindrical rod, excess cement composition flowing out around the rod was removed with an instrument, and this sample was allowed to stand still at room temperature for 30 minutes and was then immersed in distilled water. The resultant sample that had been immersed in distilled water was allowed to stand still for 24 hours inside a thermostat whose temperature was maintained at 37° C. Thus, a bonding test sample was produced. As for bonding test samples, ten samples were produced for each of the powder-liquid type resin-reinforced glass ionomer cements, and five samples were produced for each of the two paste type resin-reinforced glass ionomer cements. With respect to five samples among the ten samples of the powder-liquid type resin-reinforced glass ionomer cements, in order to evaluate bond durability, bond strength was measured after 4000 thermal cycles had been performed, with one cycle being a process for further immersing each sample in 4° C. cold water and 60° C. warm water alternately for one minute.

(3) Measurement of Bond Strength

The tensile bond strengths of the above-mentioned five bonding test samples were measured with a universal testing machine (manufactured by Shimadzu Corporation), with the crosshead speed being set at 2 mm/min, and the average value thereof was taken as tensile bond strength.

As is clear from the results of Examples 1 to 5, when the compositions of the present invention are applied as dental materials, they exhibit excellent adhesive properties.

INDUSTRIAL APPLICABILITY

Since the polymerizable monomer (A) in the present invention has a plurality of polymerizable groups and hydroxyl groups, it is useful for the applications that require curability and those that require hydrophilicity. A polymerizable composition containing this polymerizable monomer can be used for various applications including dental applications. Particularly, this composition is suitable for dental materials such as a primer, bonding material, composite resin, and cement.

The invention claimed is:

1. A composition comprising: a polymerizable monomer (A) having an unconjugated carbon chain with at least four carbon atoms bonded continuously, at least two polymerizable groups, and at least two hydroxyl groups; and a polymerizable monomer (B) having one polymerizable group and at least one hydroxyl group, wherein the polymerizable monomer (A) is a compound represented by formula (6):

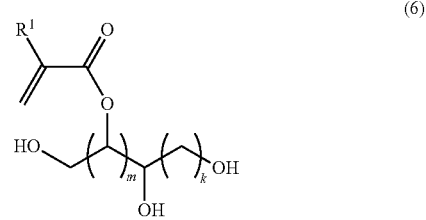

(6)

in which $R^1$ denotes a hydrogen atom or an aliphatic hydrocarbon group having 1 to 10 carbon atoms, m denotes an integer of 2 or more, k denotes an integer of 1 or more, and the sequence order of m units having an ester group and k units having a hydroxyl group is arbitrary.

2. The composition according to claim 1, wherein $R^1$ denotes an aliphatic hydrocarbon group having 1 to 10 carbon atoms.

3. The composition according to claim 1, wherein m is 2 to 5 and k is 1 to 5.

4. The composition according to claim 1, wherein the polymerizable monomer (B) is a compound represented by formula (8):

[Chemical Formula 8]

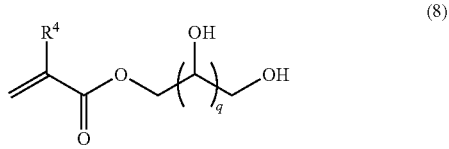

(8)

in which $R^4$ denotes a hydrogen atom or an aliphatic hydrocarbon group having 1 to 10 carbon atoms and q denotes an integer of 0 or more.

5. The composition according to claim 4, wherein q is 0 to 4.

6. The composition according to claim 4, wherein q is 0.

7. The composition according to claim 4, wherein $R^4$ is a hydrogen atom or a methyl group.

8. The composition according to claim 1, wherein 1 to 98 parts by weight of the polymerizable monomer (A) is contained in 100 parts by weight of the whole amount of polymerizable monomer components.

9. The composition according to claim 1, wherein 2 to 5000 parts by weight of the polymerizable monomer (B) is contained with respect to 100 parts by weight of the polymerizable monomer (A).

10. The composition according to claim 1, wherein 1 to 90 parts by weight of a polymerizable monomer (C) having an acidic group is further contained in 100 parts by weight of the whole amount of polymerizable monomer components.

11. The composition according to claim 1, wherein 1 to 90 parts by weight of a crosslinkable polymerizable monomer (D) is further contained in 100 parts by weight of the whole amount of polymerizable monomer components.

12. The composition according to claim 1, wherein 1 to 2000 parts by weight of a solvent (E) is contained with respect to 100 parts by weight of the whole amount of polymerizable monomer components.

13. The composition according to claim 1, wherein 0.001 to 30 parts by weight of a polymerization initiator (F) is contained with respect to 100 parts by weight of the whole amount of polymerizable monomer components.

14. The composition according to claim 1, wherein 0.001 to 30 parts by weight of a polymerization accelerator (G) is contained with respect to 100 parts by weight of the whole amount of polymerizable monomer components.

15. The composition according to claim 1, wherein 1 to 2000 parts by weight of a filler (H) is contained with respect to 100 parts by weight of the whole amount of polymerizable monomer components.

16. A dental application composition comprising the composition according to claim 1.

17. A primer composition comprising the composition according to claim 1.

18. A bonding material, comprising the composition according to claim 1.

19. A composite resin composition comprising the composition according to claim 1.

20. A cement, comprising the composition according to claim 1.

21. The composition according to claim 1, wherein $R^1$ denotes a hydrogen atom.

22. The composition according to claim 2, wherein m is 2 to 5 and k is 1 to 5.

23. The composition according to claim 5, wherein m is 2 to 5 and k is 1 to 5.

24. The composition according to claim 21, wherein m is 2 to 5 and k is 1 to 5.

* * * * *

UNITED STATES PATENT AND TRADEMARK OFFICE
CERTIFICATE OF CORRECTION

PATENT NO. : 7,977,405 B2  
APPLICATION NO. : 12/523538  
DATED : July 12, 2011  
INVENTOR(S) : Hiroshige Ishino et al.

Page 1 of 1

It is certified that error appears in the above-identified patent and that said Letters Patent is hereby corrected as shown below:

On the title page, Item (73), the Assignee Information is incorrect. Item (73) should read:

-- (73) Assignee: Kuraray Medical Inc., Kurashiki-shi (JP) --

Signed and Sealed this
Twenty-second Day of November, 2011

David J. Kappos
*Director of the United States Patent and Trademark Office*